(12) United States Patent
Cathomen et al.

(10) Patent No.: US 11,072,782 B2
(45) Date of Patent: Jul. 27, 2021

(54) CONSTRUCT FOR EPIGENETIC MODIFICATION AND ITS USE IN THE SILENCING OF GENES

(71) Applicant: Albert-Ludwigs-Universitaet Freiburg, Freiburg (DE)

(72) Inventors: Toni Cathomen, Freiburg (DE); Claudio Mussolino, Freiburg (DE); Tatjana I. Cornu, Freiburg (DE); Tafadzwa Mlambo, Freiburg (DE); Sandra Nitsch, Freiburg (DE); Jamal Alzubi, Freiburg (DE); Marianna Romito, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 401 days.

(21) Appl. No.: 15/950,403

(22) Filed: Apr. 11, 2018

(65) Prior Publication Data
US 2019/0024090 A1 Jan. 24, 2019

Related U.S. Application Data

(63) Continuation-in-part of application No. 15/657,641, filed on Jul. 24, 2017, now abandoned.

(51) Int. Cl.
| | |
|---|---|
| *C12N 9/10* | (2006.01) |
| *C12N 15/86* | (2006.01) |
| *C12N 15/63* | (2006.01) |
| *C07K 14/47* | (2006.01) |

(52) U.S. Cl.
CPC ........ *C12N 9/1007* (2013.01); *C07K 14/4703* (2013.01); *C12N 15/63* (2013.01); *C12N 15/86* (2013.01); *C12Y 201/01037* (2013.01); *C07K 2319/80* (2013.01)

(58) Field of Classification Search
CPC ............ C07K 14/4703; C07K 2319/80; C07K 2319/81; C12Y 201/01037; C12N 9/1007; C12N 15/85; C12N 15/86
See application file for complete search history.

(56) References Cited

U.S. PATENT DOCUMENTS

2003/0108880 A1* 6/2003 Rebar ................ C12N 15/8216
435/6.12

FOREIGN PATENT DOCUMENTS

| | | |
|---|---|---|
| WO | WO 2016/063264 | 4/2016 |
| WO | WO-2016063264 A1 * | 4/2016 ............. A61K 38/45 |

OTHER PUBLICATIONS

Conserved Protein Domain Family entry cd07765: KRAB_A-box, https://www.ncbi.nlm.nih.gov/Structure/cdd/cddsrv.cgi?ascbin=8 &maxaln=10&seltype=2&uid=cd07765, updated Jan. 17, 2013, printed as pp. 1/2-2/2. (Year: 2013).*
Margolin et al. Krüppel-associated boxes are potent transcriptional repression domains. Proceedings of the National Academy of Sciences, USA, vol. 91, No. 10, pp. 4509-4513, May 1994. (Year: 1994).*
Urrutia, R. KRAB-containing zinc-finger repressor proteins. Genome Biology, vol. 4, 231, Sep. 23, 2003, printed as pp. 1-8. (Year: 2003).*
Siddique et al. Targeted Methylation and Gene Silencing of VEGF-A in Human Cells by Using a Designed Dnmt3a-Dnmt3L Single-Chain Fusion Protein with Increased DNA Methylation Activity. Journal of Molecular Biology, vol. 425, pp. 479-491, 2013, including pp. 1/6-6/6 of Supplementary Information. (Year: 2013).*
Supplementary Figures for Mlambo et al. Nucleic Acids Research, vol. 46, No. 9, pp. 4456-4468, Mar. 10, 2018, Feb. 26, 2018, printed as pp. 1/13-13/13. (Year: 2018).*
Mlambo, Tafadzwa et al., "Designer Epigenome Modifiers Enable Robust and Sustained Gene Silencing in Clinically Relevant Human Cells", *Nucleic Acids Research*, 2018, pp. 1-13.
T. Mlambo et al., "Designer Epigenome Modifiers Enable Robust and Sustained Gene Silencing in Clinical Relevant Human Cells", *Nucleic Acids Research*, vol. 46 (9), pp. 4456-4468 (May 2018), including pp. 1/13-13/13 of supplementary information.

* cited by examiner

*Primary Examiner* — Jennifer Dunston
(74) *Attorney, Agent, or Firm* — Smith Patent, LLC; Chalin A. Smith

(57) ABSTRACT

Herein described is a construct for epigenomic modification of genes composed of: (a) a Krüppel-associated box zinc finger protein or homologous, (b) a DNA region capable of binding to the target gene or homologous, (c) a human DNA methyltransferase DNMT3A or homologous and (d) a murine DNA methyltransferase Dnmt3L or homologous, wherein components a), b), c) and d) are linked to each other either directly or via at least one linker. The construct is a designer epigenome modifier that can be used to silence genes coding for a protein in leukocytes that avoids the internalization of HI viruses in immune cells.

15 Claims, 16 Drawing Sheets
**Specification includes a Sequence List

SEQUENCE LISTING

```
<160> NUMBER OF SEQ ID NOS: 79

<210> SEQ ID NO 1
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: KRAB

<400> SEQUENCE: 1

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
                20                  25                  30

Thr Ala Gln Gln Ile Leu Tyr Arg Asn Val Met Leu Glu Asn Tyr Lys
            35                  40                  45

Asn Leu Val Ser Leu Gly Tyr Gln Leu Thr Lys Pro Asp Val Ile Leu
        50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

Val

<210> SEQ ID NO 2
<211> LENGTH: 543
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: fusion construct

<400> SEQUENCE: 2

Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
                20                  25                  30

Ala Thr Gly Leu Leu Val Leu Lys Asp Leu Gly Ile Gln Val Asp Arg
            35                  40                  45

Tyr Ile Ala Ser Glu Val Cys Glu Asp Ser Ile Thr Val Gly Met Val
        50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95
```

```
Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
            115                 120                 125

Asp Ala Arg Pro Lys Glu Gly Asp Arg Pro Phe Phe Trp Leu Phe
        130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
            195                 200                 205

Glu His Gly Arg Ile Ala Lys Phe Ser Lys Val Arg Thr Ile Thr Thr
            210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
            275                 280                 285

His Leu Phe Ala Pro Leu Lys Glu Tyr Phe Ala Cys Val Ser Ser Gly
            290                 295                 300

Asn Ser Asn Ala Asn Ser Arg Gly Pro Ser Phe Ser Ser Gly Leu Val
305                 310                 315                 320

Pro Leu Ser Leu Arg Gly Ser His Met Gly Pro Met Glu Ile Tyr Lys
            325                 330                 335

Thr Val Ser Ala Trp Lys Arg Gln Pro Val Arg Val Leu Ser Leu Phe
            340                 345                 350

Arg Asn Ile Asp Lys Val Leu Lys Ser Leu Gly Phe Leu Glu Ser Gly
            355                 360                 365

Ser Gly Ser Gly Gly Gly Thr Leu Lys Tyr Val Glu Asp Val Thr Asn
370                 375                 380

Val Val Arg Arg Asp Val Glu Lys Trp Gly Pro Phe Asp Leu Val Tyr
385                 390                 395                 400

Gly Ser Thr Gln Pro Leu Gly Ser Ser Cys Asp Arg Cys Pro Gly Trp
            405                 410                 415

Tyr Met Phe Gln Phe His Arg Ile Leu Gln Tyr Ala Leu Pro Arg Gln
            420                 425                 430

Glu Ser Gln Arg Pro Phe Phe Trp Ile Phe Met Asp Asn Leu Leu Leu
            435                 440                 445

Thr Glu Asp Asp Gln Glu Thr Thr Thr Arg Phe Leu Gln Thr Glu Ala
            450                 455                 460

Val Thr Leu Gln Asp Val Arg Gly Arg Asp Tyr Gln Asn Ala Met Arg
465                 470                 475                 480

Val Trp Ser Asn Ile Pro Gly Leu Lys Ser Lys His Ala Pro Leu Thr
                485                 490                 495

Pro Lys Glu Glu Glu Tyr Leu Gln Ala Gln Val Arg Ser Arg Ser Lys
            500                 505                 510
```

-continued

```
Leu Asp Ala Pro Lys Val Asp Leu Leu Val Lys Asn Cys Leu Leu Pro
        515                 520                 525

Leu Arg Glu Tyr Phe Lys Tyr Phe Ser Gln Asn Ser Leu Pro Leu
    530                 535                 540

<210> SEQ ID NO 3
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Dnmt3a

<400> SEQUENCE: 3

Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val
    290                 295                 300
```

```
<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker

<400> SEQUENCE: 4

Ser Ser Gly Asn Ser Asn Ala Asn Ser Arg Gly Pro Ser Phe Ser Ser
1               5                   10                  15

Gly Leu Val Pro Leu Ser Leu Arg Gly Ser His
            20                  25

<210> SEQ ID NO 5
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Dmnt3L

<400> SEQUENCE: 5

Met Gly Pro Met Glu Ile Tyr Lys Thr Val Ser Ala Trp Lys Arg Gln
1               5                   10                  15

Pro Val Arg Val Leu Ser Leu Phe Arg Asn Ile Asp Lys Val Leu Lys
                20                  25                  30

Ser Leu Gly Phe Leu Glu Ser Gly Ser Gly Ser Gly Gly Thr Leu
            35                  40                  45

Lys Tyr Val Glu Asp Val Thr Asn Val Val Arg Arg Asp Val Glu Lys
50                  55                  60

Trp Gly Pro Phe Asp Leu Val Tyr Gly Ser Thr Gln Pro Leu Gly Ser
65                  70                  75                  80

Ser Cys Asp Arg Cys Pro Gly Trp Tyr Met Phe Gln Phe His Arg Ile
                85                  90                  95

Leu Gln Tyr Ala Leu Pro Arg Gln Glu Ser Gln Arg Pro Phe Phe Trp
            100                 105                 110

Ile Phe Met Asp Asn Leu Leu Leu Thr Glu Asp Asp Gln Glu Thr Thr
            115                 120                 125

Thr Arg Phe Leu Gln Thr Glu Ala Val Thr Leu Gln Asp Val Arg Gly
            130                 135                 140

Arg Asp Tyr Gln Asn Ala Met Arg Val Trp Ser Asn Ile Pro Gly Leu
145                 150                 155                 160

Lys Ser Lys His Ala Pro Leu Thr Pro Lys Glu Glu Tyr Leu Gln
                165                 170                 175

Ala Gln Val Arg Ser Arg Ser Lys Leu Asp Ala Pro Lys Val Asp Leu
            180                 185                 190

Leu Val Lys Asn Cys Leu Leu Pro Leu Arg Glu Tyr Phe Lys Tyr Phe
            195                 200                 205

Ser Gln Asn Ser Leu Pro Leu
        210                 215

<210> SEQ ID NO 6
<211> LENGTH: 301
<212> TYPE: PRT
<213> ORGANISM: Artificial Sequence
```

-continued

```
<220> FEATURE:
<223> OTHER INFORMATION: Description of Artificial Sequence: Synthetic
      polypeptide
<220> FEATURE:
<223> OTHER INFORMATION: inactive Dnmt3A

<400> SEQUENCE: 6

Asn His Asp Gln Glu Phe Asp Pro Pro Lys Val Tyr Pro Pro Val Pro
 1               5                  10                  15

Ala Glu Lys Arg Lys Pro Ile Arg Val Leu Ser Leu Phe Asp Gly Ile
             20                  25                  30

Ala Thr Gly Leu Leu Val Leu Lys Asp Leu Gly Ile Gln Val Asp Arg
         35                  40                  45

Tyr Ile Ala Ser Glu Val Cys Glu Asp Ser Ile Thr Val Gly Met Val
     50                  55                  60

Arg His Gln Gly Lys Ile Met Tyr Val Gly Asp Val Arg Ser Val Thr
 65                  70                  75                  80

Gln Lys His Ile Gln Glu Trp Gly Pro Phe Asp Leu Val Ile Gly Gly
                 85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Ala Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val
    290                 295                 300

<210> SEQ ID NO 7
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TALE
<220> FEATURE:
<221> NAME/KEY: MOD_RES
<222> LOCATION: (154)..(156)
<223> OTHER INFORMATION: Any naturally occurring amino acid
```

<400> SEQUENCE: 7

Ala Pro Arg Arg Arg Ala Ala Gln Pro Ser Asp Ala Ser Pro Ala Ala
1               5                   10                  15

Gln Val Asp Leu Arg Thr Leu Gly Tyr Ser Gln Gln Gln Gln Glu Lys
            20                  25                  30

Ile Lys Pro Lys Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Lys Tyr Gln Asp Met Ile Ala
65                  70                  75                  80

Ala Leu Pro Glu Ala Thr His Glu Ala Ile Val Gly Val Gly Lys Gln
                85                  90                  95

Trp Ser Gly Ala Arg Ala Leu Glu Ala Leu Leu Thr Val Ala Gly Glu
            100                 105                 110

Leu Arg Gly Pro Pro Leu Gln Leu Asp Thr Gly Gln Leu Leu Lys Ile
        115                 120                 125

Ala Lys Arg Gly Gly Val Thr Ala Val Glu Ala Val His Ala Trp Arg
130                 135                 140

Asn Ala Leu Thr Gly Ala Pro Leu Asn Xaa Xaa Xaa Leu Thr Pro Pro
145                 150                 155                 160

Gln Gln Val Val Ala Ile Ala Ser Asn Ser Gly Gly Arg Pro Ala Leu
                165                 170                 175

Glu Ser Ile Val Ala Gln Leu Ser Arg Pro Asp Pro Ala Leu Ala Ala
            180                 185                 190

Leu Thr Gly Ser
        195

<210> SEQ ID NO 8
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TALE N-terminal region

<400> SEQUENCE: 8

Ala Pro Arg Arg Arg Ala Ala Gln Pro Ser Asp Ala Ser Pro Ala Ala
1               5                   10                  15

Gln Val Asp Leu Arg Thr Leu Gly Tyr Ser Gln Gln Gln Gln Glu Lys
            20                  25                  30

Ile Lys Pro Lys Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Lys Tyr Gln Asp Met Ile Ala
65                  70                  75                  80

Ala Leu Pro Glu Ala Thr His Glu Ala Ile Val Gly Val Gly Lys Gln
                85                  90                  95

Trp Ser Gly Ala Arg Ala Leu Glu Ala Leu Leu Thr Val Ala Gly Glu
            100                 105                 110

Leu Arg Gly Pro Pro Leu Gln Leu Asp Thr Gly Gln Leu Leu Lys Ile
        115                 120                 125

```
Ala Lys Arg Gly Gly Val Thr Ala Val Glu Ala Val His Ala Trp Arg
        130                 135                 140

Asn Ala Leu Thr Gly Ala Pro Leu Asn
145                 150
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DNA binding domain

<400> SEQUENCE: 9
tgaccatata cttatgtca                                               19

<210> SEQ ID NO 10
<211> LENGTH: 578
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: binding domain

<400> SEQUENCE: 10

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240
```

```
Pro Glu Gln Val Val Ala Ile Ala Ser Asn Gly Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Glu Gln Val Val Ala Ile Ala Ser Asn Gly Gly Gly Lys Gln Ala
        515                 520                 525

Leu Glu Thr Val Gln Arg Leu Leu Pro Val Leu Cys Gln Ala His Gly
    530                 535                 540

Leu Thr Pro Gln Gln Val Val Ala Ile Ala Ser His Asp Gly Gly Lys
545                 550                 555                 560

Gln Ala Leu Glu Thr Val Gln Ala Leu Leu Pro Val Leu Cys Gln Ala
                565                 570                 575

His Gly

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: binding domain

<400> SEQUENCE: 11
ttgaaactgg acttacact                                                  19
```

<210> SEQ ID NO 12
<211> LENGTH: 578
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: binding domain

<400> SEQUENCE: 12

```
Leu Thr Pro Gln Gln Val Val Ala Ile Ala Ser Asn Gly Gly Gly Lys
  1               5                  10                  15

Gln Ala Leu Glu Thr Val Gln Arg Leu Leu Pro Val Leu Cys Gln Ala
             20                  25                  30

His Gly Leu Thr Pro Glu Gln Val Val Ala Ile Ala Ser Asn Asn Gly
         35                  40                  45

Gly Lys Gln Ala Leu Glu Thr Val Gln Arg Leu Leu Pro Val Leu Cys
     50                  55                  60

Gln Ala His Gly Leu Thr Pro Glu Gln Val Val Ala Ile Ala Ser Asn
 65                  70                  75                  80

Ile Gly Gly Lys Gln Ala Leu Glu Thr Val Gln Arg Leu Leu Pro Val
                 85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser Asn Asn Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Ile Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser His
            340                 345                 350
```

-continued

```
Asp Gly Gly Lys Gln Ala Leu Glu Thr Val Gln Arg Leu Pro Val
        355                 360                 365
Leu Cys Gln Ala His Gly Leu Thr Pro Gln Gln Val Val Ala Ile Ala
    370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Gly Gly Gly Lys Gln Ala Leu Glu Thr Val Gln Arg
            420                 425                 430
Leu Leu Pro Val Leu Cys Gln Ala His Gly Leu Thr Pro Glu Gln Val
        435                 440                 445
Val Ala Ile Ala Ser Asn Ile Gly Gly Lys Gln Ala Leu Glu Thr Val
    450                 455                 460
Gln Arg Leu Leu Pro Val Leu Cys Gln Ala His Gly Leu Thr Pro Gln
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
            500                 505                 510
Pro Glu Gln Val Val Ala Ile Ala Ser Asn Ile Gly Gly Lys Gln Ala
        515                 520                 525
Leu Glu Thr Val Gln Arg Leu Leu Pro Val Leu Cys Gln Ala His Gly
    530                 535                 540
Leu Thr Pro Gln Gln Val Val Ala Ile Ala Ser His Asp Gly Gly Lys
545                 550                 555                 560
Gln Ala Leu Glu Thr Val Gln Ala Leu Leu Pro Val Leu Cys Gln Ala
                565                 570                 575
His Gly
```

```
<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: binding domain

<400> SEQUENCE: 13

Leu Thr Pro Pro Gln Gln Val Val Ala Ile Ala Ser Asn Ser Gly Gly
1               5                   10                  15

Arg Pro Ala Leu Glu
            20

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: binding domain
```

<400> SEQUENCE: 14

Ser Ile Val Ala Gln Leu Ser Arg Pro Asp Pro Ala Leu Ala Ala Leu
1               5                   10                  15

Thr Gly Ser

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 15
tgaccatata cttatgtca                                              19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 16
taaccatata cttatctca                                              19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 17
tgaacatata cttatgtca                                              19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 18
tgaccatata cctatctca                                              19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

```
<400> SEQUENCE: 19
tcaccatata catatatca                                              19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 20
tcaccatata catatatca                                              19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 21
tcaccatata catatatca                                              19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 22
tgaacatata cttatctca                                              19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 23
taaccatata tttatatca                                              19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 24
taaccatata tttatatca                                              19
```

```
<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 25
tagccatata cttatatca                                                19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 26
tgaccatata cttatgtca                                                19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 27
tgaacatata cttatgtca                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 28
agacaatata cttatgtca                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 29
tcactatata cttatgtca                                                19

<210> SEQ ID NO 30
<211> LENGTH: 19
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: target sequence

<400> SEQUENCE: 30
ttacaatata cttatgtca                                                19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 31
tgagaatata cttatgtca                                                19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 32
tgattatata cttatgtca                                                19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 33
tgagcatcta cttatgtca                                                19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 34
tgaccctcta cttatgtca                                                19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: target

<400> SEQUENCE: 35
tgatcatatc cttatgtca                                                    19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 36
ttaccatata gttatgtca                                                    19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 37
tgtccatata tttatgtca                                                    19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 38
tgaccaaatt cttatgtca                                                    19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 39
tgatcatata gttatgtca                                                    19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target
```

```
<400> SEQUENCE: 40
tgactatata tttatgtca                                                 19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 41
tgaccatttg cttatgtca                                                 19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 42
tgaccaaata tttatgtca                                                 19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 43
tgaccatcta tttatgtca                                                 19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 44
ttaccatata catatgtca                                                 19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 45
tgtccatata catatgtca                                                 19
```

```
<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 46
tgtccatata catatgtca                                               19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 47
tgaccataca tttatgtca                                               19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 48
tgaccgtata catatgtca                                               19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 49
tgagcatata ctgatgtca                                               19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 50
tgaccatatg tttatgtca                                               19

<210> SEQ ID NO 51
<211> LENGTH: 19
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 51
tgaccacata ctgatgtca                                                 19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 52
tgaccataca ctgatgtca                                                 19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 53
ttaccatata cttttgtca                                                 19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 54
tgatcatata cttctgtca                                                 19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 55
tgatcatata cttttgtca                                                 19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<220> FEATURE:
<223> OTHER INFORMATION: target

<400> SEQUENCE: 56
tgaccttata cttctgtca                                                    19

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 57
tgaccatcta cttgtgtca                                                    19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 58
tggccatata cttaagtca                                                    19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 59
tgaccaaata cttaggtca                                                    19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 60
tgaccatata catgtgtca                                                    19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 61
taaccatata cttatctca                                           19

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 62
tgaacatata cttatctca                                           19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 63
tgaccataaa cttatttca                                           19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 64
tgaccatatc cttatttca                                           19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 65
tgaccatatt cttatctca                                           19

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 66
tgaccatata cctatctca                                           19

```
<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 67
tgacaatata cttatgaca                                                19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 68
tgaccatatc cttatggca                                                19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 69
tgaccatata attatgcca                                                19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 70
tgagcatata cttatgtaa                                                19

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 71
tgaccatgta cttatgtaa                                                19

<210> SEQ ID NO 72
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 72
tgaccatgta cttatgtaa                                                   19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 73
tgaccatgta cttatgtaa                                                   19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 74
tgaccatatt cttatgtaa                                                   19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 75
tgaccatata gttatgtaa                                                   19

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 76
tgaccatata cgtatgtaa                                                   19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: target

<400> SEQUENCE: 77
tgactatata cttatgtct                                                    19

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 78
tgaccatatt cttatgtct                                                    19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target

<400> SEQUENCE: 79
tgaccatata cttttgtga                                                    19
```

CONSTRUCT FOR EPIGENETIC MODIFICATION AND ITS USE IN THE SILENCING OF GENES

SEQUENCE LISTING

The instant application contains a Sequence Listing that has been submitted in ASCII format via EFS-Web and is hereby incorporated by reference in its entirety. Said ASCII copy, created on Jan. 19, 2018, is named LNK_185US_ST25.txt and is 45,761 bytes in size.

FIELD OF INVENTION

The present invention relates to gene silencing by epigenetics. Epigenetic marks are stable heritable traits that are not caused by changes in the DNA sequence. Epigenetic changes refer to changes in the chromosome that affect gene activity, in particular transcription and the expression of genes.

BACKGROUND OF INVENTION

Epigenetic changes of the genome comprise changes in DNA methylation and histone modification. Gene expression may for example be controlled through the action of proteins that bind to regulatory regions of the DNA and alter the expression of genes. Such interactions may be influenced by epigenetic modifications. Epigenetic changes may last through several cell divisions and for multiple generations even though they do not involve changes in the underlying DNA sequence of the organism. It is important to note that gene silencing is specific for the targeted gene. In general it is not an inhibition of a certain function of a cell. Usually the target gene is coding for a protein and the successful silencing prevents the formation of the protein of interest. Nowadays there are many different types of methods known to achieve reduction of gene expression, for example by RNA interference. The present invention makes, however, use of epigenetic changes, such as DNA methylation and histone modifications, to achieve control of target gene expression.

In alternative strategies not used in the present invention, therapeutic benefit can be obtained by inactivating a gene whose expression is deleterious for example because of the presence of a mutation that renders the resulting protein dominant negative. This can be achieved by using designer nucleases tailored to introduce a double stranded DNA break (DSB) in a sequence of choice (i.e. the coding sequence of the gene to inactivate). Subsequent harnessing of the error prone DNA repair mechanism non-homologous end-joining (NHEJ), will result in the introduction of insertion or deletion mutations at the DSB site with consequent functional inactivation of the target gene. A similar strategy can be used to provide the cells with a novel function. For example, cells can be made resistant to HIV by inactivating one of the co-receptor required by the virus for entering into the cells. Designer nucleases capable of inducing the DSB in the sequence of choice (e.g. the HIV co-receptors CCR5 or CXCR4) were used.

Other alternative strategies may be chosen to inactivate a gene of interest which rely either on driving the degradation of the mRNA encoding for the protein of interest (i.e. by means of RNA interference or RNAi) or by impeding the transcription of the target gene using single stranded oligodeoxynucleotides, gene silencers or artificial transcription factors. Even though data obtained with all these different approaches are promising and have paved the way for clinical trials particularly in the field of HIV therapy, several aspects still pose hurdles in further developing these technologies. In particular, low efficiency of RNAi especially for repressing highly expressed genes and off-targeting of designer nucleases still represent major drawbacks to overcome for safe entering of these technologies in clinical practice. In addition, interference with endogenous cellular mechanisms, particularly in the case of RNAi, may lead to toxic adverse events.

Epigenetic modifications comprise two main categories, namely DNA methylation and histone modifications. In vertebrates DNA methylation occurs almost exclusively in the context of CpG dinucleotides and most CpGs in the genome may be methylated whereby 5-methylcytosine is formed. Vertebrate CpG islands (CGIs) are short interspersed DNA sequences that deviate significantly from the average genomic pattern by being CpG-rich and predominantly non-methylated. Many CpG-rich areas are localized to promoters or enhancers which control transcription initiation, and dense CpG methylation of these areas is usually associated with silencing of gene expression. CpG methylation is achieved through the action of DNA methyltransferases, namely DNMT3A, DNMT3B and DNMT3L that induce de novo methylation of a cytosine base to methylated 5-methylcytosine.

The DNMT3A, DNMT3B and DNMT3L methyltransferases are responsible for de novo methylation and the DNA Methyltransferase DNMT1 is responsible for the maintenance of methylation through cellular divisions resulting in the maintenance of the methylation pattern in the course of cell division.

Furthermore, the histones on which the DNA is bound are subject to many different post-translational modifications including acetylation, methylation, phosphorylation and ubiquitination. Such post-translational modifications occur primarily at specific positions within the amino-terminal histone tails. The methylation of certain amino acids in the amino-terminal region of histones may have different effects. Whereas for example the tri-methylation of lysine at position 4 and arginine at position 17 of histone H3 leads to an activation of transcription, the contrary effect, namely an inhibition of transcription may be caused by a tri-methylation of lysine at position 9. Concerning histone H4 the methylation of arginine at position 3 leads to an activation of transcription whereas a methylation of lysine at position 20 leads to an inhibition of transcription. The methylation pattern of the histones is therefore also decisive whether certain genes are expressed or not.

The human genome contains about 30,000 genes including at least 2,000 loci encoding transcription factor proteins. The so-called C2H2 or Krüppel-type zinc finger is the most common DNA-binding motif found in eukaryotic transcription factor proteins. At least one-third of mammalian Krüppel-type zinc finger proteins include an effector motif called the Krüppel-associated box or KRAB which serves to recruit histone deacetylase complexes to regions surrounding the DNA-binding sites (Huntley et al., Genome Research (2006), 669).

The KDM2 family of histone demethylases includes KDM2A and KDM2B. KDM2A can act on mono- and di-methylated H3K36 and tri-methylated H3K4 (H3 is histone 3 and K36 or K4 stand for lysine at position 4 and 36, respectively). KDM2B acts only on mono- and di-methylated H3K36. In many eukaryotes, the KDM2A protein contains a CXXC zinc finger domain capable of binding to non-methylated CpG islands. It is currently thought that KDM2A proteins may bind to many gene regulatory elements without the aid of sequence specific transcription factors.

Chemical modifications to histone proteins and cytosine bases provide heritable epigenetic information that is not encoded in the nucleotide sequence. Although such epigenetic modifications do not change the primary sequence of DNA, such modifications are inherited from the parent cell to the daughter cells over several cell cycles which results in the permanent and stable silencing of certain genes.

SUMMARY OF THE INVENTION

The invention described herein provides means that can be efficiently used to stably silence a target gene in human cell lines and in particular in therapeutically relevant primary cells which may be derived e.g. from blood of human specimens. Preferably such primary cells may be any human primary cells whereby human leukocytes are particularly preferred. The invention provides a combination of different effector domains in one molecule that allows the silencing of a target gene through the specific editing of the epigenetic marks governing the expression of the chosen gene.

The present invention provides a construct (herein also designated as "designer epigenome modifier", "DEM") suitable for the epigenetic modification of genes whereby said construct comprises sequences corresponding to:
a) a Krüppel-associated box zinc finger protein or homologous,
b) a DNA binding domain capable of binding to the target gene (also designated as TALE-based DNA binding domain) or homologous,
c) a DNA methyltransferase DNMT3A of human origin or homologous, and
d) a DNA methyltransferase Dnmt3L of murine origin or homologous.

The components a), b), c) and d) are either directly linked to each other or they are linked via a linker structure. The term "homologous" means that in the sequence of the nucleic acid or the protein encoded thereby must not necessarily be identical with the precise sequences as disclosed in the present application. The term "homologous" comprises also such sequences which have variations of up to 10%, preferably up to 5% and especially preferred up to 3% of the precisely disclosed sequences. Even with the replaced base or amino acids, respectively, the function of the original sequence must be maintained.

The construct of the present invention exerts its direct activity on the genomic DNA level which as a consequence induces a subsequent block of target gene transcription and translation. The DNA methyltransferases DNMT3A and Dnmt3L methylate the cysteine residues. DNA binding domains which are capable of binding to the target gene are derived from transcription activator-like effector proteins (TALE). The DNA binding domains may, depending on the nature of the construct, be a protein or peptide, a DNA sequence or an RNA sequence. In a preferred embodiment, the TALE-based DNA binding domain binds to a cis-regulatory region, and the other components of the construct may exert their activity particularly on the target gene since they are in spatial proximity of the target gene of interest.

The construct of the present invention may have a proteinaceous nature or be a nucleic acid. Also mixtures of proteins/peptides and nucleic acids are possible, whereby such constructs may be synthesized ex vivo by chemical synthesis or a combination of chemical synthesis and recombinant technique.

Since the epigenetic modification of the target locus induced by the construct of the present invention involves the enzymatic methylation of cytosine residues and recruits the necessary factors for the enzymatic modification of the N-terminal parts of histones, it is evident that the construct exerts its activity on the protein level. To introduce complex protein molecules such as a construct of the present invention into target cells may, however, be difficult in particular when the introduction into cells of solid organs is desired. Therefore, the construct of the present invention may also be present in the form of a polynucleotide coding for the construct. Such a polynucleotide comprises genes coding for components a)-d). It is an essential aspect of the present invention that a construct comprises all four components which are linked together in a single entity.

When the construct of the present invention is used as a protein, such a fusion protein is preferably prepared in a suitable host. For the application in humans the constructs may be produced in yeast cells, in bacterial cells, in insect cells or in mammalian cell cultures depending on the specific requirements of the expressed proteins.

In a preferred embodiment, the construct is used on a nucleic acid level. The advantage of nucleic acid constructs is that the information can be introduced more easily into the target cells on the nucleic acid level and the target organism/host cell produces the construct with the own cellular machinery. The information coding for the construct may be introduced into the cell either in the form of a messenger RNA usable by the target cell, or with the help of a vector which may provide either transiently or permanently the construct translated with the machinery of the target cell.

When transcribed from the nucleic acid, the messenger RNA is translated to protein. Linkers may for example be simple polyglycine stretches which connect for example a DNA methyltransferase DNMT3A with a DNA methyltransferase Dnmt3L. It is known that the successful construction of fusion proteins relies on the proper choice of a protein linker for the connection of two domains. In general, linkers can be classified into three groups, namely flexible, rigid and cleavable linkers. Flexible linkers are generally composed of small, non-polar or polar residues such as glycine, serine or threonine. The most common linker is the $Gly_4Ser_{(n)}$ linker, whereby n is an integer of 1 to preferably 10. More rigid linkers include polyprolin motifs. The preferred linkers are selected in accordance with the sterical orientation of the single components of the construct. It is preferred to bring the single constructs in an optimal position where they can exert their activity for the modification of the target gene.

In a preferred embodiment, the construct of the present invention is inserted into the target cells with the help of a vector. Depending on the target cells the vector may be a plasmid, a viral vector or another suitable carrier of foreign genetic information which is able to transfer the gene construct into the target cell. The construct may be integrated into the genome possibly at several sites or the construct may be maintained only temporarily in the target cell.

In a preferred embodiment, the vectors of the present invention are derived from a lentivirus, an adenovirus or adeno-associated virus. Such vectors are able to transport the genetic information of the construct of the present invention into the target cell. In the target cell the information is transcribed and translated to the construct with the machinery of the target cell.

In preferred embodiments, the construct of the present invention is transferred into the target cell by appropriate means, e.g. electroporation or lipofection in the form of an mRNA molecule. The mRNA molecule contains the genetic information for the construct of the present invention. The genetic information contained within the messenger RNA can be directly translated into a protein. Usually the mRNA contains besides the information required for the construct according to the present invention also a 5'-cap which is preferably a 7-methylguanosine cap. Furthermore, the mRNA usually has a polyadenosine stretch at the 3'-end whereby also a 3'-untranslated region (UTR) may be present. Such UTRs are sections of the mRNA before the start codon and/or after the stop codon which are not translated. These regions are present in the mature mRNA and provide superior properties to the mRNA like increased stability and enhanced translational efficiency.

In a preferred embodiment, the construct may be a nucleic acid in the form of a DNA or an RNA, preferably mRNA whereby the nucleic acids may be modified depending on the desired use. The nucleotides can be stabilized against degradation, for example by DNAses or RNAses, by using chemically modified nucleic acids.

In a preferred embodiment, the information coding for the DEM is introduced into the target cell in the form of an mRNA. It has been observed that the efficiency of expression was substantially increased when using mRNA molecules as compared to the use of plasmid DNA. It is expected that by using mRNA the expression of the DEMs occurs only for a short period of time.

The construct of the present invention can be used in a method for silencing a certain target gene. In such method the construct is introduced into the target cell and the gene of interest is silenced by epigenetic modification of the gene. In a particularly preferred embodiment the method is used for silencing a receptor in human primary cells, preferably leukocytes. By silencing the co-receptors CCR5 and CXCR4 in human T cells, the human immunodeficiency virus can no longer attach to the target cells (leukocytes) and this modification of the leukocytes provides resistance against infection with human immunodeficiency viruses.

In a preferred embodiment of the invention, the construct can be used to generate human T cells broadly resistant to infection with human immunodeficiency virus (HIV) by single or multiple HIV co-receptor silencing. In an especially preferred embodiment the invention allows the stable silencing of the HIV co-receptors CCR5 and CXCR4 in human T cells. Since the invention induces a change in the epigenetic status of the target locus, it is particularly advantageous for multiplexing (i.e. targeting multiple genes with a single administration) as compared to more invasive techniques such as genome editing using designer nucleases that, in case of multiplexing, can induce deleterious genomic rearrangements.

In further embodiments, the invention can be applied to silence any gene in the human genome with the aim for example to provide resistance to other viruses, such as hepatitis B virus (HBV), or to silence mutated genes whose product has a dominant negative effect on the normal gene like in the case of certain STAT3 mutations in Hyper-IgE syndrome.

In further embodiments, the invention can be used to silence relevant genes in compartmentalized organs, such as Rhodopsin or vascular endothelial growth factor (VEGF) genes in the human eye, to potentially cure blindness disorders like Retinitis Pigmentosa, proliferative diabetic retinopathy, neovascular age-related macular degeneration, and retinopathy of prematurity. In general, the invention can be applied to silence any selected gene for therapeutic purpose by altering the epigenetic marks that define the expression status of the target gene.

In another embodiment, the construct of the present invention may be used to replace the function of endogenous regulators (i.e. endogenous DNA methyltransferases or transcription factors) in case of malfunction due to natural mutations and/or as a consequence of therapies, such as inactivation due to e.g. insertional mutagenesis following gene therapy. In those embodiments the construct can be used to regulate the expression of endogenous genes, that have lost their regulation or whose regulation is disturbed due to a malfunction of the endogenous regulator (i.e. the endogenous mutated DNA methyltransferase or any other regulator as a transcription factor that is no longer functional).

In a further embodiment, the constructs of the present invention can be used to study the chromatin architecture within a cell with the aim to develop novel assays to profile the off-target activity of targeted platforms. Chromatin within the nucleus is highly structured and DNA locations which are far away considering a linear chromatin molecule may be spatially close to each other due to DNA bending. When for example the construct of the present invention binds to a certain position on a certain chromosome, an epigenetic modification in a different position can occur. This may be interpreted as a consequence of the chromatin spatial organization that may bring two positions in close proximity that on a linear molecule are far apart. This effect allows for the study of chromatin tridimensional architecture within the nucleus of a cell through the use of the present invention and can be used to predict off-targeting of e.g. designer nucleases, at sites that share no similarity at the DNA level but are cleaved simply because they are spatially closer to the cleavage domain of a targeted nuclease.

The present invention allows for controlling the expression of a target gene upon delivery of a single molecule in the target cell which means that all components of the construct are present in a single molecule or that the gene coding for the present invention is contained within a single nucleic acid sequence. This is particularly appealing for commercialization since a single-molecule product reduces the costs of manufacturing and the time-consuming procedures to obtain authorization for in human use.

Moreover, the invention is highly versatile allowing for the easy exchange of effector domains to remove epigenetic marks that block transcription thereby allowing the reactivation of target genes. This is particularly useful in the field of cancer therapy to reactivate silenced tumor suppressor genes.

Gene therapy aims at curing human disorders by delivering new genes into the cell of a patient in order to revert the diseased phenotype. Depending on the nature of the underlying defect, the new genetic material may complement a missing function in the host cell, inactivate a deleterious gene or provide a new function to the target cell. In the last thirty years, gene therapy has been successfully used to cure patients affected by different immune defects caused by mutations capable to inactivate the function of key genes in the hematopoietic system. Providing the target cells with a DNA fragment encoding for the missing gene product may lead to the restoration of the defect and subsequent cure of the patient. This is typically achieved by delivering the exogenous DNA using a viral vector that, upon stable integration into the host cell genome, drives the expression of the missing protein.

The present invention relates in some embodiments to methods of treatment of a patient wherein the silencing of a gene helps to cure or eliminate a disease. One of the preferred examples of such methods is the silencing of a gene coding for the co-receptors CCR5 and/or CXCR4 in human T cells in isolated T cells. Human T cells can be isolated by well-known methods from human plasma, e.g. by leukapheresis. The isolated human T cells are then brought into contact with a suitable construct for epigenome modification as described herein. The uptake of the construct may be enhanced by means which improve the efficiency of uptake like e.g. from virus-derived vectors and/or by electroporation, lipofection or by embedding or adhering the construct to suitable uptake enhancing material.

An efficient and stable gene silencing is gathering interest. This is based on the alteration of epigenetic marks at a target locus of interest by using epigenetic modifiers that can be used both to activate dormant genes and to silence expressed genes. This is achieved by using effector domains capable of changing the DNA methylation status and/or modifying the histone tails in order to favor the establishment of active or repressed chromatin. In principle, this approach may lead to the establishment of chromatin states that are stable over cell division and are thereby inherited by the daughter cells. This represents a major advantage particularly when compared to RNAi that needs the continuous expression of the silencing molecule to repress the target gene expression.

Another important aspect is related to off-target effects. Unlike designer nucleases which introduce an off-targeted DNA double strand break that may initiate a cascade of events leading to deleterious genomic rearrangements, the off-target activity of epigenome modifiers is likely to be silent if occurring far from promoter or enhancer regions, providing an important advantage in terms of safety. Two major limitations that need to be overcome in order to render this approach amenable for clinical utilization are the ability to introduce modifications that are maintained over cell division for long term and in particular the efficiency to control gene expression in primary human cells. To date, the most efficient methods developed still fail either to prove long lasting effects on gene expression or to efficiently modulate the expression of an endogenous gene in clinically relevant primary cells, such as human T cells. Hence, there is still a major need for means which improve epigenome editing, which render these means more robust and efficient and which prepare the ground towards their application in human therapy.

This invention provides improved means (construct and its use) capable to induce stable silencing of endogenous human genes in cell lines and, in particular, in primary T cells with an effect that is maintained over time during cell proliferation.

The means provided in the present invention can be used in the treatment of patients. It is in some diseases desirable to silence one or more genes stably for the duration of several cell divisions. In such methods of treatment the construct (DEM) is either transferred ex vivo to target cells of the patient to be treated. A preferred example thereof is the silencing of a co-receptor required for the entering of human immunodeficiency viruses into T cells. Alternatively, the DEM can be introduced into the patient in vivo, whereby it exerts its activity in the target cells.

The construct of the invention is herein also designated as "designer epigenome modifier" (DEM) that combines, in a single molecule, a high specific DNA binding domain (DBDs) derived from bacterial transcription activator-like effectors (TALEs), the Krüppel-associated box domain (KRAB) that is able to recruit the scaffold protein KRAB-associated protein 1 (KAP1) that in turn is suggested to regulate transcription through the induction of histone modifications as deacetylation or tri-methylation and the DNA methyltransferases 3a and 3L for efficient CpG methylation.

The single molecule nature of DEMs allows for the presence of the three effector domains (i.e. KRAB, DNMT3A and Dnmt3L) at the same time at the target locus thereby promoting a strong signal to initiate the cascade of events leading to gene silencing. Importantly, the single molecule DEM allows for the development of cost effective protocols to induce gene silencing in clinically relevant cells since it relies on the production and validation of a single reagent (i.e. an mRNA molecule that contains the coding sequence of a DEM).

In a particular preferred embodiment, a construct was used whereby the "KRAB" nucleotide coded for a protein having the following amino acid sequence:

(SEQ ID NO: 1)
MDAKSLTAWSRTLVTFKDVFVDFTREEWKLLDTAQQILYRNVMLENYKNL

VSLGYQLTKPDVIRLRLEKGEEPWLVEREIHQETHPDSETAFEIKSSV

In preferred embodiments, the KRAB is derived from KOX1 or ZNF10. As NCBI Reference Sequence NM 015394.4 may be mentioned.

In a further preferred embodiment, the DNA methyltransferases DNMT3A (human) and Dnmt3L (murine) were linked with a connecting stretch whereby the protein encoded by the genes has the following sequence:

(SEQ ID NO: 2)
NHDQEFDPPKVYPPVPAEKRKPIRVLSLFDGIATGLLVLKDLGIQVDRYI

ASEVCEDSITVGMVRHQGKIMYVGDVRSVTQKHIQEWGPFDLVIGGSPCN

DLSIVNPARKGLYEGTGRLFFEFYRLLHDARPKEGDDRPFFWLFENVVAM

GVSDKRDISRFLESNPVMIDAKEVSAAHRARYFWGNLPGMNRPLASTVND

KLELQECLEHGRIAKFSKVRTITTRSNSIKQGKDQHFPVFMNEKEDILWC

TEMERVFGFPVHYTDVSNMSRLARQRLLGRSWSVPVIRHLFAPLKEYFAC

VSSGNSNANSRGPSFSSGLVPLSLRGSHMGPMEIYKTVSAWRKQPVRVLS

LFRNIDKVLKSLGFLESGSGSGGGTLKYVEDVTNVVRRDVEKWGPFDLVY

GSTQPLGSSCDRCPGWYMFQFHRILQYALPRQESQRPFFWIFMDNLLLTE

DDQETTTRFLQTEAVTLQDVRGRDYQNAMRVWSNIPGLKSKHAPLTPKEE

EYLQAQVRSRSKLDAPKVDLLVKNCLLPLREYFKYFSQNSLPL

The N-terminal part of the construct coding for the amino acid sequence:

(SEQ ID NO: 3)
NHDQEFDPPKVYPPVPAEKRKPIRVLSLFDGIATGLLVLKDLGIQVDRY

IASEVCEDSITVGMVRHQGKIMYVGDVRSVTQKHIQEWGPFDLVIGGSP

CNDLSIVNPARKGLYEGTGRLFFEFYRLLHDARPKEGDDRPFFWLFENV

VAMGVSDKRDISRFLESNPVMIDAKEVSAAHRARYFWGNLPGMNRPLAS

TVNDKLELQECLEHGRIAKFSKVRTITTRSNSIKQGKDQHFPVFMNEKE

DILWCTEMERVFGFPVHYTDVSNMSRLARQRLLGRSWSVPVIRHLFAPL

KEYFACV codes for human DNMT3A. The active catalytic site (ENV) is underlined.

The linker has the following sequence:

(SEQ ID NO: 4)
SSGNSNANSRGPSFSSGLVPLSLRGSH and the gene coding for murine Dnmt3L has the following amino acid sequence:

(SEQ ID NO: 5)
MGPMEIYKTVSAWKRQPVRVLSLFRNIDKVLKSLGFLESGSGSGGGTLKY
VEDVTNVVRRDVEKWGPFDLVYGSTQPLGSSCDRCPGWYMFQFHRILQYA
LPRQESQRPFFWIFMDNLLLTEDDQETTTRFLQTEAVTLQDVRGRDYQNA
MRVWSNIPGLKSKHAPLTPKEEEYLQAQVRSRSKLDAPKVDLLVKNCLLP
LREYFKYFSQNSLPL.

In the present construct, a murine DNA methyltransferase (Dnmt3L) has been used. It is, however, also possible to use alternatively human DNMT3L methyltransferases when the construct is humanized. Corresponding sequences are highly homologous to the Dnmt3L derived from mouse and have a sequence identity of at least 90% with the murine sequence. In the experiments a mutant sequence coding for inactive Dnmt3A (dDnmt3A) was used for control purposes. The gene codes for the amino acid sequence:

(SEQ ID NO: 6)
NHDQEFDPPKVYPPVPAEKRKPIRVLSLFDGIATGLLVLKDLGIQVDRYI
ASEVCEDSITVGMVRHQGKIMYVGDVRSVTQKHIQEWGPFDLVIGGSPCN
DLSIVNPARKGLYEGTGRLFFEFYRLLHDARPKEGDDRPFFWLF<u>ANV</u>VAM
GVSDKRDISRFLESNPVMIDAKEVSAAHRARYFWGNLPGMNRPLASTVND
KLELQECLEHGRIAKFSKVRTITTRSNSIKQGKDQHFPVFMNEKEDILWC
TEMERVFGFPVHYTDVSNMSRLARQRLLGRSWSVPVIRHLFAPLKEYFAC
V.

The amino acid sequence ANV is underlined and represents the inactive catalytic center. In the active DNMT3A the sequence is also underlined and has the following amino acid sequence: "ENV". It is obvious that small mutations may have a dramatic effect in particular when the catalytic center is affected. In other areas, however, the genes can easily be mutated and amino acid changes do not negatively affect the activity of the construct of the present invention. The single components of the present invention may comprise therefore also homologous sequences of the components a), b), c) and d) whereby the sequences have an identity of at least 50%, preferably of at least 60%, 70%, 80% or 90% and most preferred of at least 98%.

The preferred TALE (transcription-activator-like effector)-based DNA binding domain had the following sequence:

(SEQ ID NO: 7)
APRRRAAQPSDASPAAQVDLRTLGYSQQQQEKIKPKVRSTVAQHHEALVG
HGFTHAHIVALSQHPAALGTVAVKYQDMIAALPEATHEAIVGVGKQWSGA
RALEALLTVAGELRGPPLQLDTGQLLKIAKRGGVTAVEAVHAQRNALTGA
PLN<u>xxx</u>LTPPQQVVAIASNSGGRPALESIVAQLSRPDPALAALTGS comprising the following parts:

(SEQ ID NO: 8)
APRRRAAQPSDASPAAQVDLRTLGYSQQQQEKEKPKVRSTVAQHHEALVG
HGFTHAHIVALSQHPAALGTVAVKYQDMIAALPEATHEAIVGVGKQWSGA
RALEALLTVAGELRGPPLQLDTGQLLKIAKRGGVTAVEAVHAWRNALTGA
PLN which represents the TALE N-terminal region.

xxx: This can be any TALE-based DNA binding domain targeting a sequence of choice as in the following examples:

A CCR5-specific TALE-based DNA binding domain binding targeting the DNA sequence (SEQ ID NO:9) tgac-catatacttatgtca (with the amino acids responsible for the binding to single nucleotides underlined) may be selected from the following sequences:

(SEQ ID NO: 10)
LTPQQVVAIAS<u>NN</u>GGKQALETVQRLLPVLCQAHGLTPEQVVAIAS<u>NI</u>GGK
QALETVQRLLPVLCQAHG

LTPEQVVAIAS<u>HD</u>GGKQALETVQRLLPVLCQAHGLTPEQVVAIAS<u>HD</u>GGK
QALETVQRLLPVLCQAHG

LTPEQVVAIAS<u>NI</u>GGKQALETVQRLLPVLCQAHGLTPEQVVAIAS<u>NG</u>GGK
QALETVQRLLPVLCQAHG

LTPQQVVAIAS<u>NI</u>GGKQALETVQALLPVLCQAHGLTPEQVVAIAS<u>NG</u>GGK
QALETVQALLPVLCQAHG

LTPEQVVAIAS<u>NI</u>GGKQALETVQRLLPVLCQAHGLTPQQVVAIAS<u>HD</u>GGK
QALETVQRLLPVLCQAHG

LTPQQVVAIAS<u>NG</u>GGKQALETVQRLLPVLCQAHGLTPQQVVAIAS<u>NG</u>GGK
QALETVQRLLPVLCQAHG

LTPEQVVAIAS<u>NI</u>GGKQALETVQRLLPVLCQAHGLTPEQVVAIAS<u>NG</u>GGK
QALETVQRLLPVLCQAHG

LTPQQVVAIAS<u>NN</u>GGKQALETVQRLLPVLCQAHGLTPEQVVAIAS<u>NG</u>GGK
QALETVQRLLPVLCQAHG

LTPQQVVAIAS<u>HD</u>GGKQALETVQALLPVLCQAHG

A CXCR4-specific TALE-based DNA binding domain binding to the DNA sequence (SEQ ID NO:11) ttgaaactggacttacact (with the amino acids responsible for the binding to single nucleotides underlined) may be selected from the following sequences:

(SEQ ID NO: 12)
LTPQQVVAIAS<u>NG</u>GGKQALETVQRLLPVLCQAHGLTPEQVVAIAS<u>NN</u>GGK
QALETVQRLLPVLCQAHG

LTPEQVVAIAS<u>NI</u>GGKQALETVQRLLPVLCQAHGLTPEQVVAIAS<u>NI</u>GGK
QALETVQRLLPVLCQAHG

LTPEQVVAIAS<u>NI</u>GGKQALETVQRLLPVLCQAHGLTPEQVVAIAS<u>HD</u>GGK
QALETVQRLLPVLCQAHG

LTPQQVVAIAS<u>NG</u>GGKQALETVQALLPVLCQAHGLTPEQVVAIAS<u>NN</u>GGK
QALETVQALLPVLCQAHG

LTPEQVVAIAS<u>NN</u>GGKQALETVQRLLPVLCQAHGLTPQQVVAIAS<u>NI</u>GGK
QALETVQRLLPVLCQAHG

LTPQQVVAIAS<u>HD</u>GGKQALETVQRLLPVLCQAHGLTPQQVVAIAS<u>NG</u>GGK
QALETVQRLLPVLCQAHG

LTPEQVVAIAS<u>NG</u>GGKQALETVQRLLPVLCQAHGLTPEQVVAIAS<u>NI</u>GGK
QALETVQRLLPVLCQAHG

-continued
LTPQQVVAIAS<u>HD</u>GGKQALETVQRLLPVLCQAHGLTPEQVVAIAS<u>NI</u>GGK
QALETVQRLLPVLCQAHG LTPQQVVAIAS<u>HD</u>GGKQALETVQALLPVLCQAHG The stretch LTPPQQVVAIASNSGGRPALE (SEQ ID NO:13) is the 17,5 repeat and SIVAQLSRPDPALAALTGS (SEQ ID NO:14) is the C-terminal linker.

It should be noted that variations of the above-mentioned constructs (SEQ ID NO:1 to SEQ ID NO:14) may comprise slight modifications. The homology of such modifications is in the area of about 80% to 99% homology, preferably 95% to 99.5% homology. This means that in such modifications 0% to 20% and preferably 0% to 5% of the amino acids may be replaced by other amino acids. It goes without saying that the modification shall not affect essential parts of the sequences which are essential for the function of the single components like e.g. the catalytic center.

The invention is disclosed in more detail in the Examples and the Figures which show the summary of the experimental results and the preferred embodiments of the invention.

BRIEF DESCRIPTION OF THE FIGURES

FIG. 1A shows a scheme of a designer epigenome modifier including the different components indicated on the right side in the legend. FIG. 1A shows four constructs, whereby, however, only the construct at the bottom of FIG. 1A (indicated as DEM) represents an embodiment of the present invention. The other constructs in the first three lines are embodiments already known and not covered by the present invention. In the first line the DNA-binding domain (TALE-DBD) is connected via a protein linker to KRAB to form a transient repressor (K). In the second and third line the DNA-binding site (TALE-DBD) is connected via linkers either to functional DNMT3A and Dnmt3L or to inactive dDNMT3a and Dnmt3L DNA methyltransferase to form a targeted methyltransferase (ΔK-DEM) or an inactive effector used as negative control (ΔK-dDEM).

FIG. 1B explains the principle of the invention. Upon delivery into the target cells, the DNA binding portion (TALE-DBD) will direct the DEM (construct) to a specific target site in the promoter (or any other regulatory element) of the target gene leading to the methylation of the neighboring CpG di-residues and the deacetylation of neighboring histone tails. As a consequence, the target gene of interest will be silenced. Since the modifications are inherited to the daughter cells, the silencing is permanent.

FIG. 2A shows schematically an eGFP (green fluorescent protein as indicator), an expression cassette driven by a minimal cytomegalovirus (minCMV) promoter and a fragment (400 bp in length) of the proximal CCR5 promoter which is randomly integrated in the genome of HEK293T cells using lentiviral vectors. The CCR5 promoter is relevant for the expression of an HIV co-receptor. When this gene is silenced in human T lymphocytes or macrophages, the co-receptor required by the virus can no longer be expressed and these leukocytes become resistant against HIV.

FIG. 2B shows the reporter cell line harboring the expression cassette shown in FIG. 2A which is transfected with mRNA coding for the indicated DEM using Lipofectamine. As a result of DEM activity, CpGs are methylated and eGFP is silenced. The decrease of GFP expressing cells is measured over time by flow cytometry. The effect of various constructs with regard to the expression of green fluorescent protein was measured. The following constructs targeting the CCR5 promoter were used:

| | |
|---|---|
| ΔK-dDEM #6 | Control. Inactive DEM, lacking the KRAB domain and harboring the inactive dDNMT3A |
| K #3 | Control. Construct harboring only the KRAB without DNA methyltransferase targeting position #3 on the CCR5 promoter |
| DEM #3 | According to invention: Construct harboring the KRAB domain and the active DNMT3A with Dnmt3L targeting position #3 on the CCR5 promoter |
| ΔK-DEM #6 | Control. Construct lacking the KRAB but harboring an active DNMT3A and Dnmt3L |
| ΔK-DEM #6 + K #3 | Control. Split construct. One construct harboring only the KRAB binding to position 3 (K) and one construct lacking the KRAB but harboring the active DNMT3A and Dnmt3L binding to position 6. Position 3 and 6 are two sites on the CCR5 promoter. |
| K #6 | Control. Construct harboring only the KRAB without DNA methyltransferase targeting position #6 on the CCR5 promoter |
| DEM #6 | According to invention: Construct harboring the KRAB domain and the active DNMT3A with Dnmt3L targeting position #6 on the CCR5 promoter |

Figure 2A:
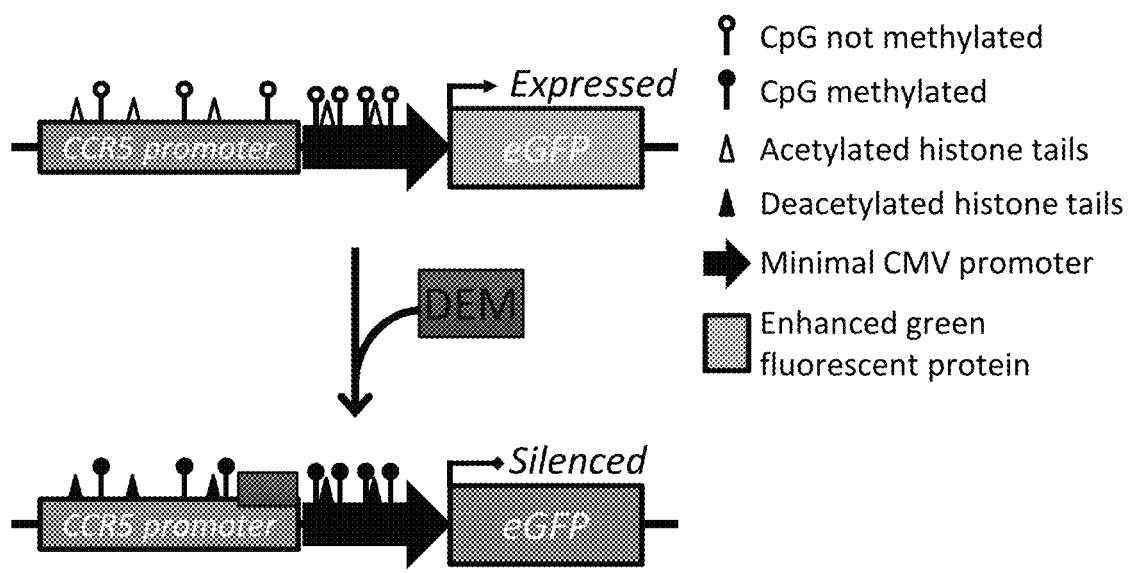
FIGS. 2A-2D depict the activity of CCR5-specific DEMs.
Figure 2B:
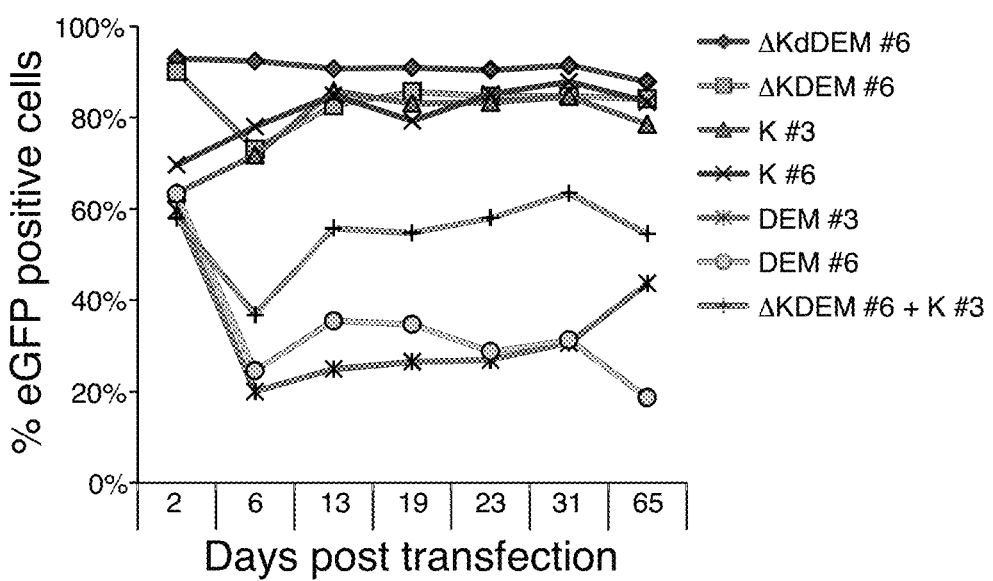
Figure 2C:
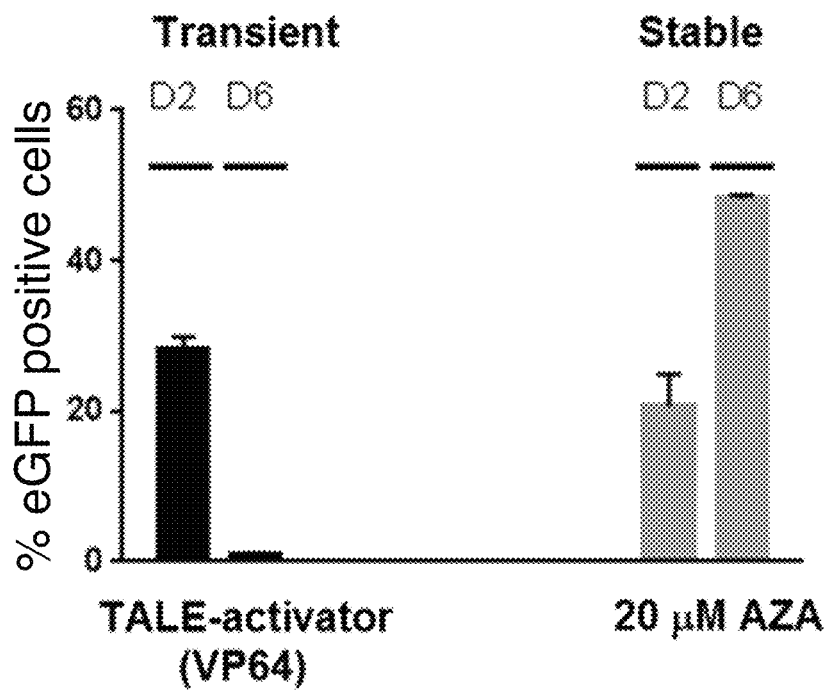

FIG. 2C shows reporter cells transfected with DEM #6 from day 31 which were further manipulated with the aim of reactivating eGFP expression. Histogram shows the % of eGFP positive cells upon delivery of a transient transcriptional activator or a drug (5-AZA) that stably demethylates CpGs resulting in stable reactivation of eGFP expression.

The left part of FIG. 2C shows the expression of enhanced green fluorescent protein (eGFP) after transient transfection on day 2 (D2) and day 6 (D6). The right-hand part of FIG. 2C shows the effect of the drug 5-AZA at the same time points.

Figure 2D:
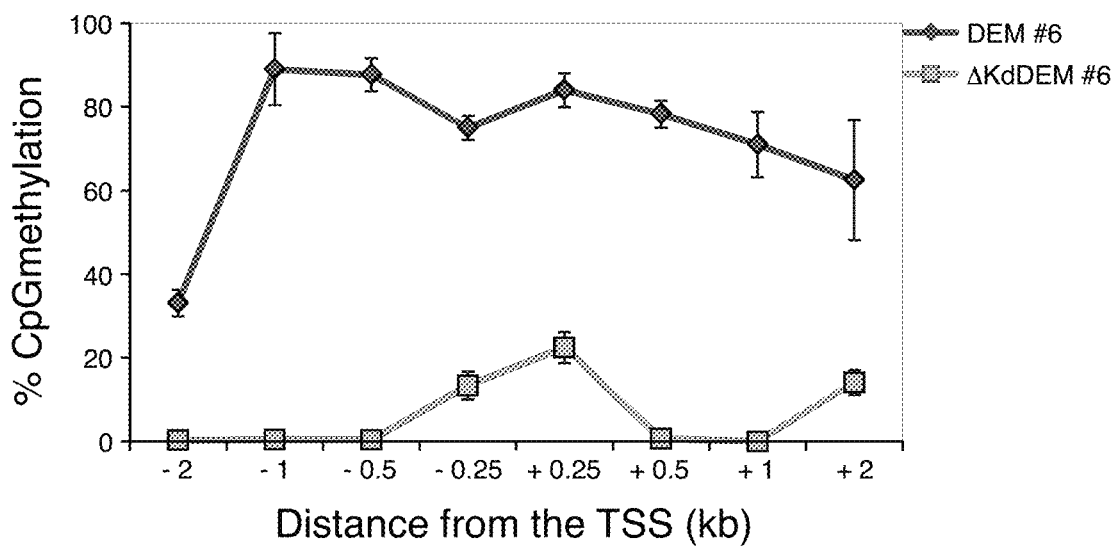

FIG. 2D shows the extent of CpG methylation induced by the construct of the present invention as is measured in the reporter cell line one month after the delivery of the indicated construct by sequencing of bisulfite converted genomic DNA.

Figure 3A:
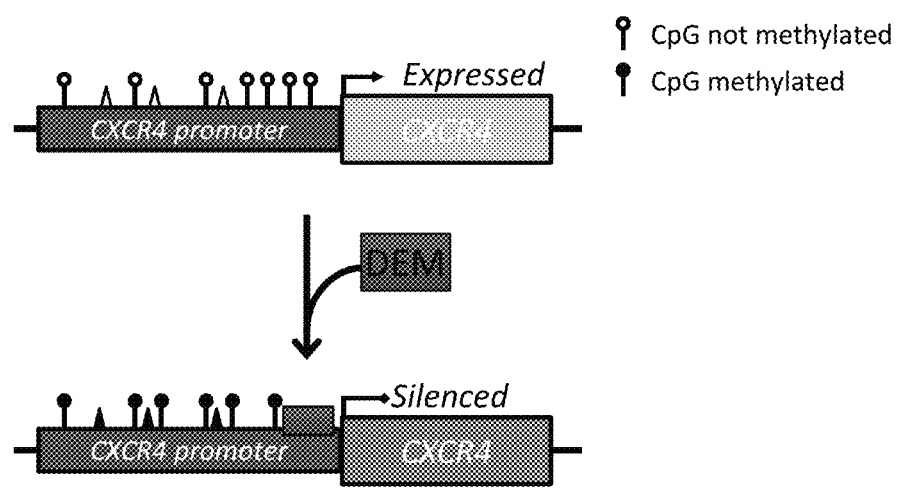
Figure 3B:
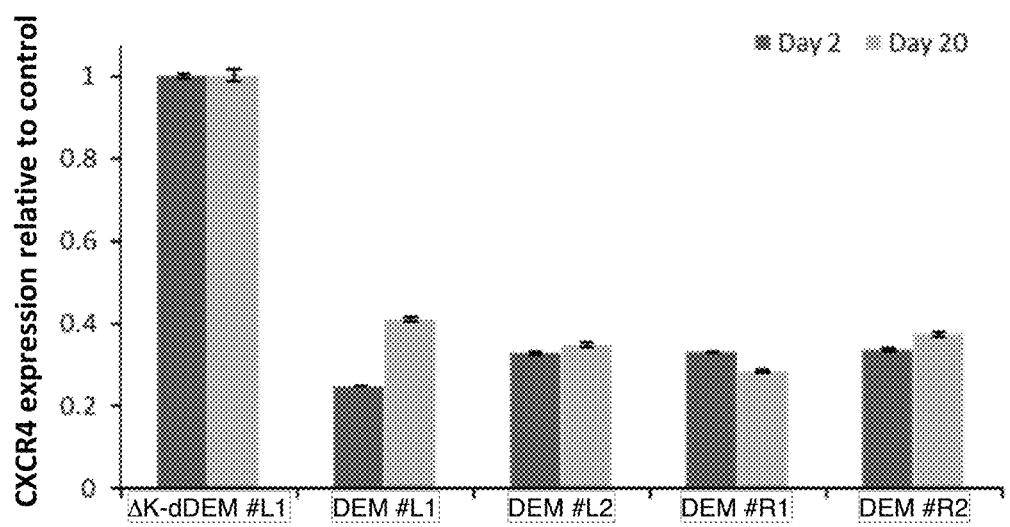
Figure 3C:
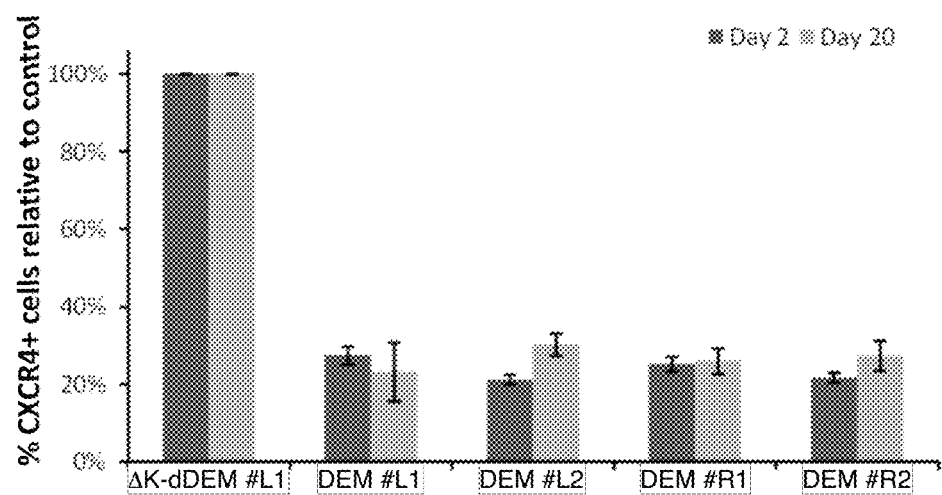

FIGS. 3A-3C depict the activity of CXCR4-specific DEMs.

FIG. 3A shows schematically the CXCR4 gene including the promoter region. Upon DEM binding, the consequent CpG methylation and deacetylation of neighboring histone tails leads to CXCR4 silencing.

FIG. 3B shows the expression levels of the CXCR4 gene which were measured in HEK293T cell line via quantitative RT-PCR (TaqMan) at the indicated time points upon transfection of mRNA encoding the indicated CXCR4-specific DEMs. The histogram shows the extent of CXCR4 gene silencing as compared to the samples transfected with mRNA coding for the inactive ΔK-dDEM. The gene expression levels are normalized to the housekeeping gene B2M.

FIG. 3C shows the CXCR4 protein levels measured by flow cytometry. The histogram shows the extent of CXCR4 positive cells as compared to the samples transfected with mRNA encoding for the inactive ΔK-dDEM.

Figure 4A:
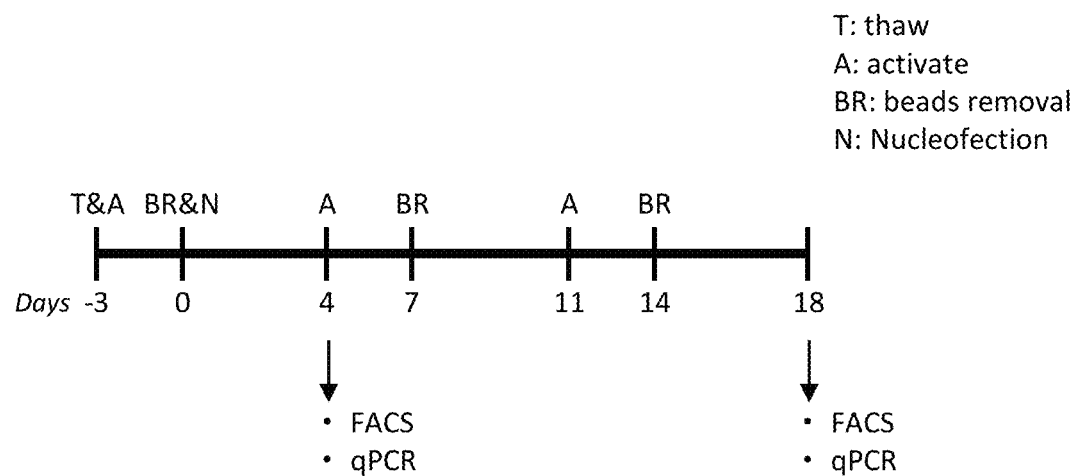
Figure 4B:
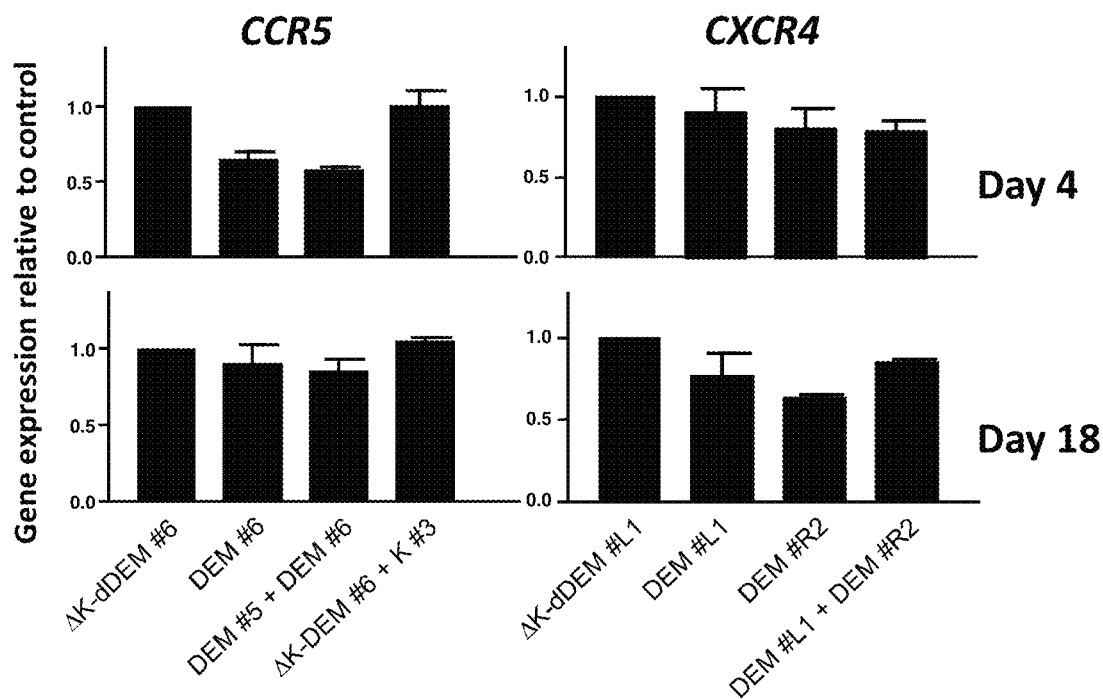
Figure 4C:
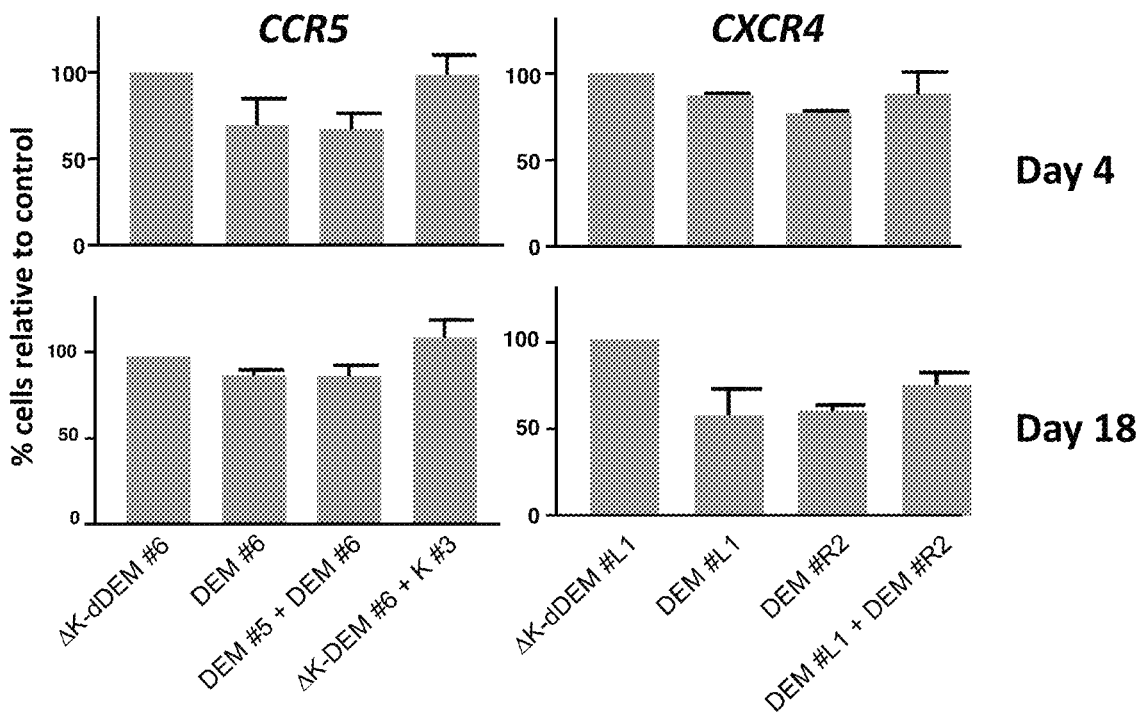

FIGS. 4A-4C depict the activity of DEMs in primary T cells.

FIG. 4A shows a time line of the experiment. Human CD4+ cells isolated from normal donors were thawed and activated with beads conjugated with antibodies recognizing CD28, CD3 and CD2 for three days. Subsequently, beads were removed and cells were transfected with mRNA encoding the indicated DEMs via nucleofection. Cells were re-activated every seven days and samples were collected for analysis (FACS and qPCR) on the indicated days (1).

FIG. 4B shows the expression levels of CCR5 and CXCR4 genes which were measured in CD4+ T cells at the indicated time points upon nucleofection via quantitative RT-PCR (TaqMan). The histograms show CCR5 and CXCR4 gene expression levels as compared to the samples transfected with mRNA encoding the inactive ΔK-dDEM #6 or ΔK-dDEM #L1, respectively. The gene expression levels are normalized to the housekeeping gene B2M.

FIG. 4C shows CCR5 and CXCR4 protein levels measured by flow cytometry. The histograms show the extent of CCR5 and CXCR4 positive T cells as compared to the samples transfected with mRNA encoding for the inactive ΔK-dDEM #6 or ΔK-dDEM #L1, respectively.

Figure 5A:
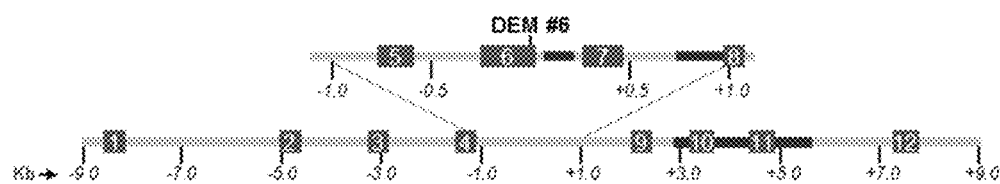
Figure 5B:
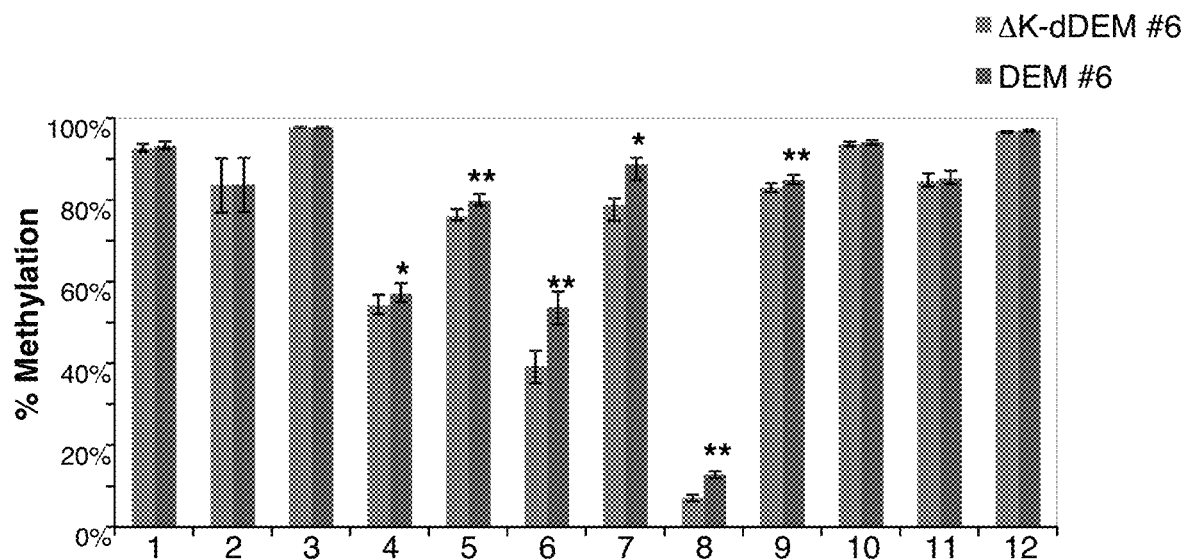
Figure 5C:
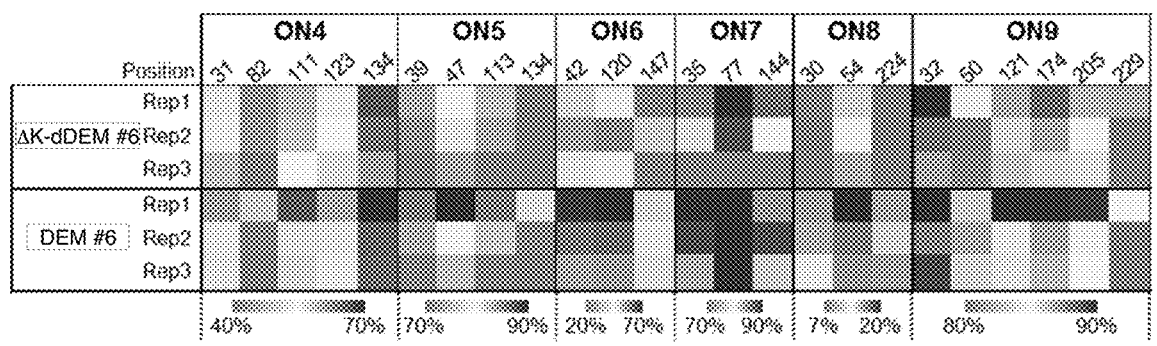

FIGS. 5A-5C depict the extent of CpG methylation induced by DEM in primary human T cells.

FIG. 5A shows a scheme of the CCR5 locus (grey) with exons highlighted. The regions amplified from bisulfite converted genomic DNA extracted from primary human T cells and analyzed via next generation sequencing are depicted with number 1-12. Relative distance from the DEM #6 binding site is shown.

FIG. 5B shows the extent of CpG methylation which was assessed via next generation sequencing of the amplicons indicated in (A) from three independent experiments. The histogram shows the % of CpG methylation as ratio between total and methylated CpGs in the samples nucleofected either with the inactive ΔK-dDEM #6 or the DEM #6, respectively.

FIG. 5C shows the extent of CpG methylation obtained from three independent experiments as heat map for a subset of the amplicons analyzed in B. The color ranges from light grey (basal methylation) to black (maximum methylation). The position of the CpG within the amplicon is indicated. (Student's t-test *p<0.05; **p<0.01).

Figure 6A:
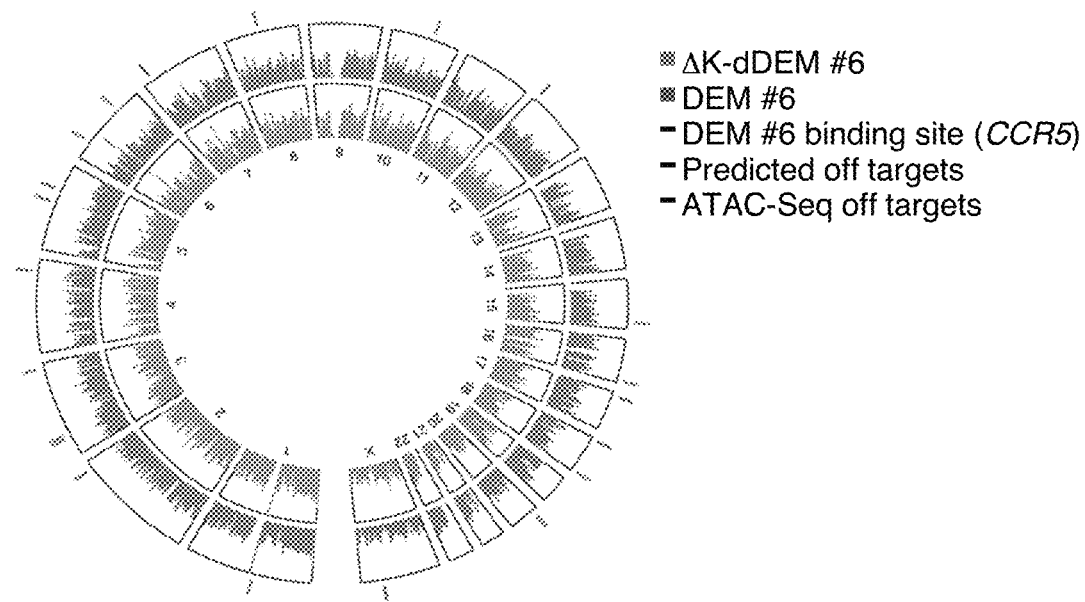
Figure 6B:
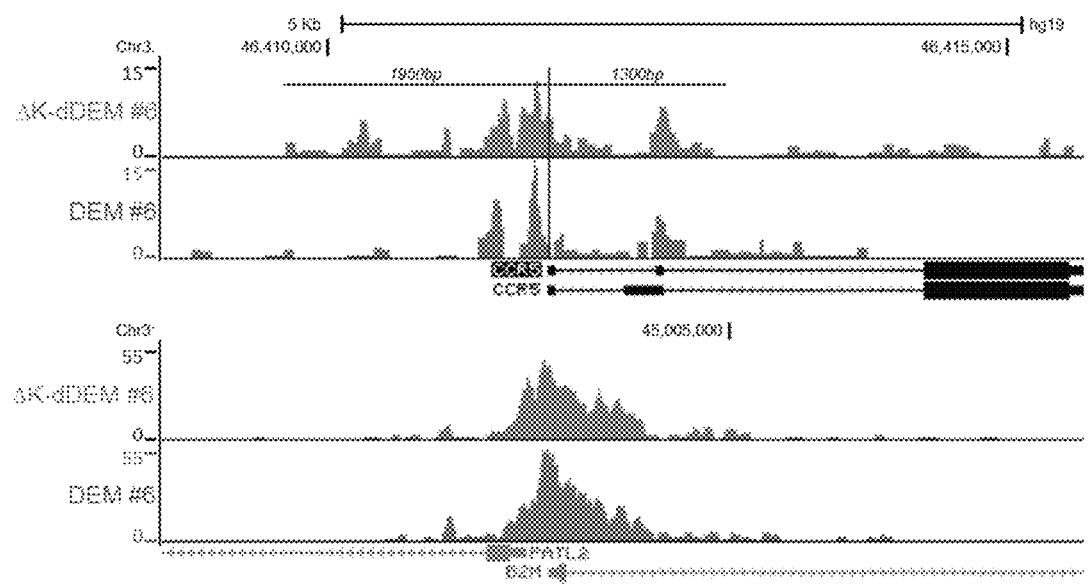

FIGS. 6A and 6B depict the off-target activity of DEM measured via ATAC-seq in primary human T cells.

FIG. 6A is a circle plot illustrating the whole genome accessibility profile resulting from ATAC-seq data combined from two independent experiments in which primary human T cells were nucleofected with the inactive ΔK-dDEM #6 (outer circle) or the DEM #6 (inner circle), respectively.

The DEM #6 binding site in CCR5 promoter is indicated with a line. Potential off-targets predicted via online tools (Table 1) or retrieved from ATAC-seq results are depicted.

FIG. 6B shows exemplary ATAC-seq data showing the reduced accessibility at the CCR5 locus as a lower ATAC-seq read counts (Upper panel). As a control, the lower panel shows the ATAC-seq read counts at the housekeeping gene locus B2M. The DEM #6 binding site is indicated with a vertical black line and the numbers in italics within the track indicate the size window of the area with reduced chromatin accessibility.

Figure 7A:
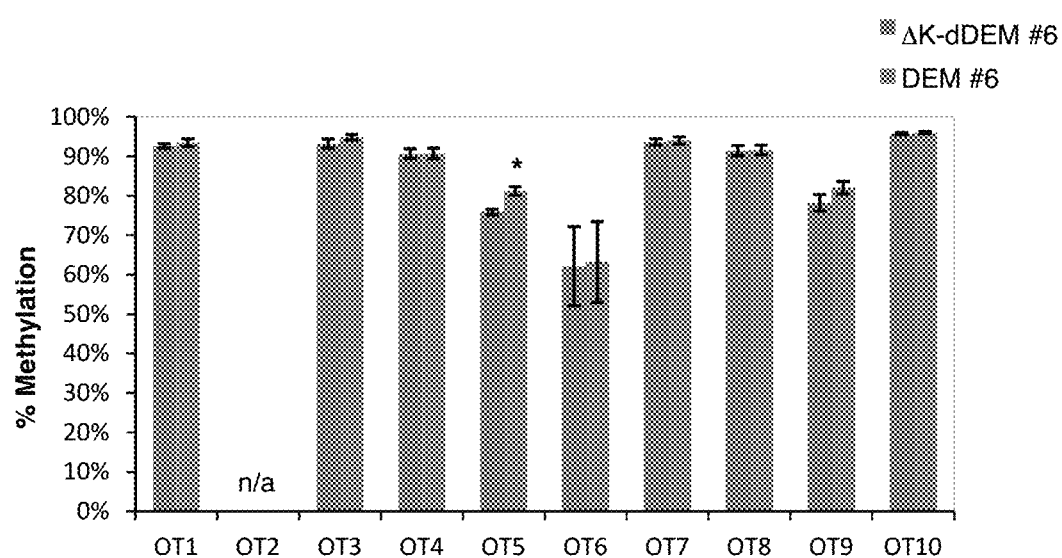
Figure 7B:
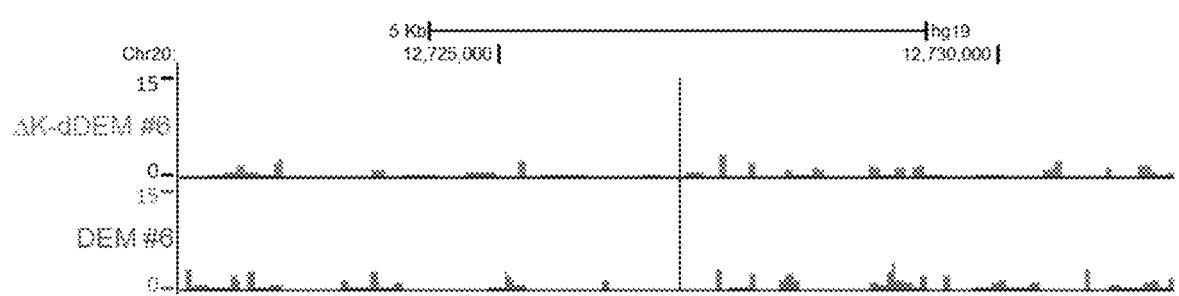

FIGS. 7A and 7B depict the off-target activity of DEM measured via next generation sequencing in primary human T cells.

FIG. 7A shows the extent of CpG methylation induced by the DEM at potential off-target (OT) sites identified with TAL Effector Nucleotide Targeter 2.0 and measured via next generation sequencing. A 300 bp amplicon centered on the potential binding site was amplified from bisulfite converted genomic DNA isolated from primary human T cells four days post nucleofection and sequenced via next generation sequencing. The histogram shows the % of CpG methylation as ratio between total and methylated CpGs in the samples nucleofected either with the inactive ΔK-dDEM #6 or the DEM #6 respectively. PCR amplification at off-target 2 was not successful. (Student's t-test *p<0.05).

FIG. 7B shows ATAC-seq data showing low accessibility at the intergenic region centered on the OT5. The potential DEM #6 off-target binding site is indicated with a vertical black line.

Figure 8A:
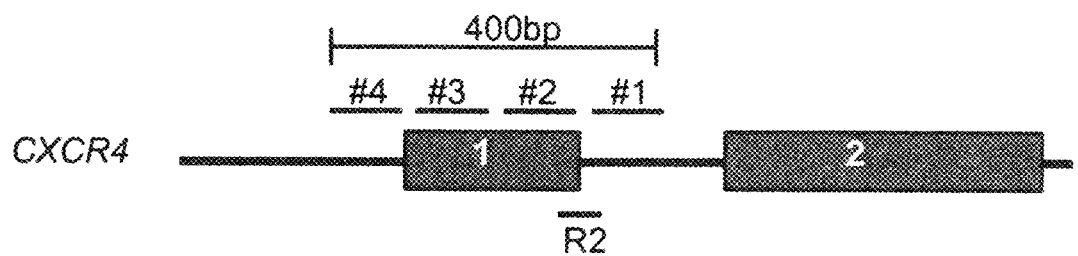
Figure 8B:
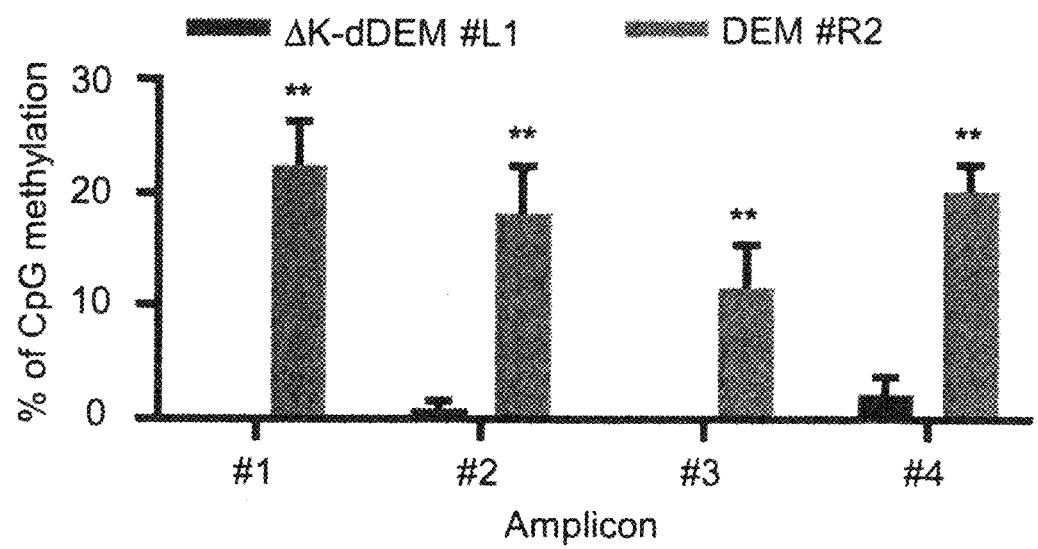

FIGS. 8A and 8B depict the effect of the CXCR4-specific DEM in HEK293T cells at the CXCR4 locus. The active epigenetic effector (DEM #R2) resulted in significantly enhanced methylation as compared to the inactive DEM (ΔK-dDEM #L1).

FIG. 8A schematically represents the CXCR4 locus with the four amplicons investigated for the extent of CpG methylation indicated in scale and numbered from #1 to #4.

FIG. 8B graphically depicts the level of CpG methylation in cells receiving the active or inactive DEM respectively. Statistical significance was calculated with a two-tailed, paired Student's t-test (*P<0.05; **P<0.01).

Figure 9:
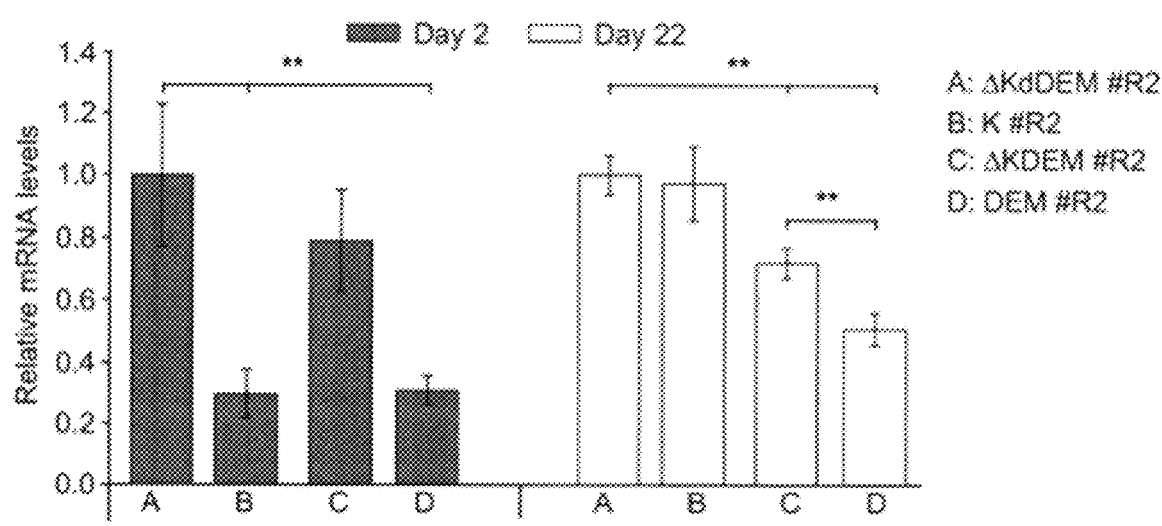

FIG. 9 depicts the results of the comparative experiment described in Example 8 in which the activities of CXCR4-specific effectors were measured.

The different effectors targeting the CXCR4 promoter used in the experiments of Example 8 were as follows:

| A | ΔKdDEM #R2 | Control. Inactive DEM, lacking the KRAB domain and harboring the inactive dDNMT3A |
|---|---|---|
| B | K # R2 | Control. Construct harboring only the KRAB without DNA methyltransferase targeting position #R2 on the CXCR4 promoter |
| C | ΔKDEM #R2 | Control. Construct lacking the KRAB but harboring an active DNMT3A and Dnmt3L |
| D | DEM #R2 | According to invention: Construct harboring the KRAB domain and the active DNMT3A with Dnmt3L targeting position #R2 on the CXCR4 promoter |

Figure 10A:
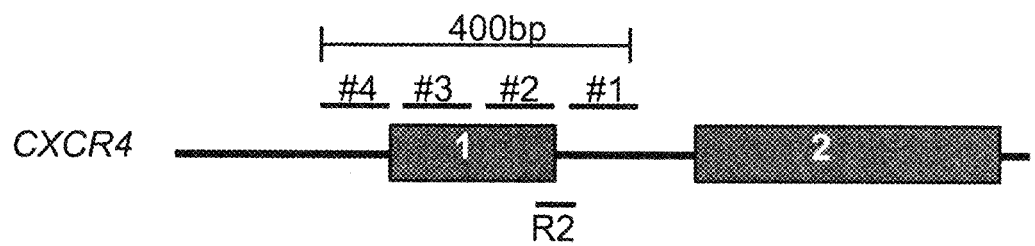
Figure 10B:
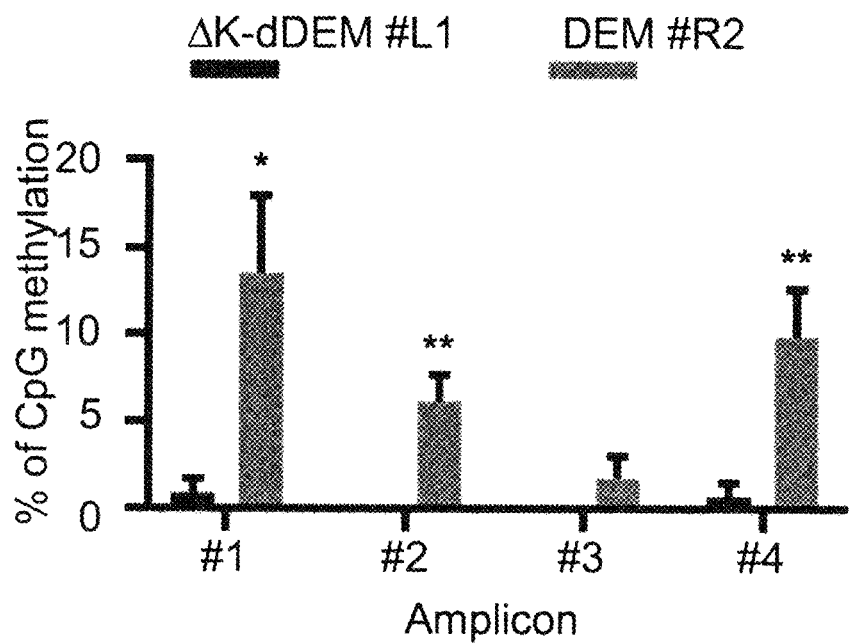

FIGS. 10A and 10B depict the CXCR4 methylation following treatment with either an inactive (ΔK-dDEM #L1) or an active (DEM #R2) epigenetic effector.

FIG. 10A schematically represents the CXCR4 locus with the four amplicons investigated for the extent of CpG methylation indicated in scale and numbered from #1 to #4.

FIG. 10B graphically depicts the level of CpG methylation in primary human T cells receiving the active or inactive DEM, respectively. Statistical significance was calculated with a two-tailed, paired Student's t-test (*P<0.05; **P<0.01).

Figure 11A:
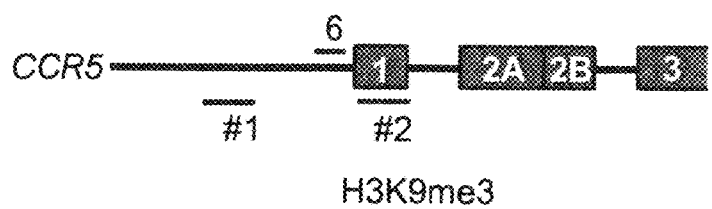
Figure 11B:
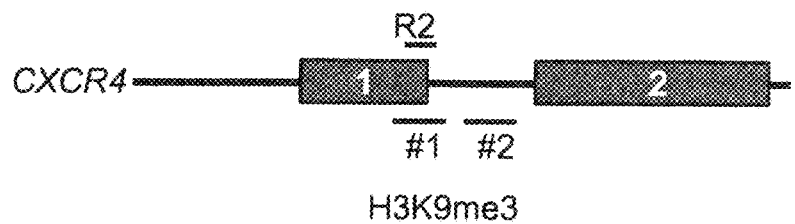
Figure 11C:
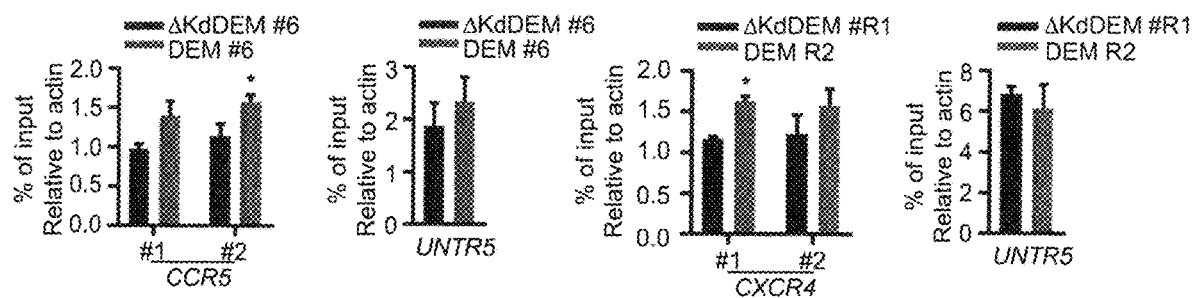

FIGS. 11A-11C depict the results of the experiments described in Example 10.

FIGS. 11A and 11B schematically depict the deposition of the repressive epigenetic mark H3K9me3 in close proximity of the CCR5-specific DEM #6 (FIG. 11A) or CXCR4-specific DEM #R2 (FIG. 11B) binding sites, respectively.

FIG. 11C graphically depicts the results of the CCR5 and CXCR4 chromatin immunoprecipitation (ChIP) experiments described in Example 10, expressed as the percentage of input relative to actin.

Figure 12:
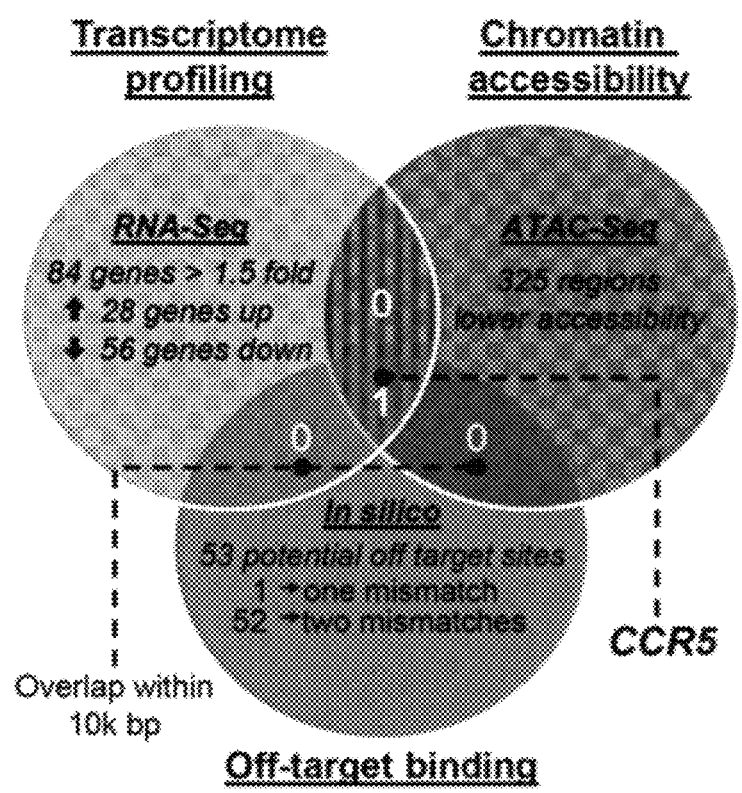

FIG. 12 is a VENN diagram depicting the overlap between ATAC-seq, RNA-sequences and in silico off-target sites predicted via COSMID (Table 2).

The number of overlapping sites is indicated. Overlap with computational prediction of off-target sites is restricted to hits within 10-kb distance from the annotated transcription start sites (TSS) of the 84 de-regulated genes identified via RNA-seq analysis or from about 325 regions of lower chromatin accessibility resulting from ATAC-seq analysis, respectively.

DETAILED DESCRIPTION OF THE PREFERRED EMBODIMENTS

The following abbreviations were used:
DEM: designer epigenome modifier
KRAB: krüppel-associated box
ZNF10: zinc finger protein 10
KOX1: zinc finger protein KOX1
DNMT3A: DNA methyltransferases member 3a (Human)
dDNMT3A: inactive or 'dead' DNA methyltransferases member 3a (Human)
Dnmt3L: DNA methyltransferases member 3L (Murine)
TALE: transcription activator-like effector
DBD: DNA binding domain
CRISPR: clustered, regularly interspaced, short palindromic repeats
Cas9: Cas9 endonuclease
dCas9: inactive or 'dead' Cas9 endonuclease
gRNA: guide RNA
bp: DNA base pairs
kbp: DNA kilo base pairs (1000 bp)
mRNA: messenger RNA
LV: lentivirus
IDLV: integrase-defective lentiviral vector
AAV: adeno-associated virus
CXCR4 gene: C—X—C chemokine receptor type 4

Example 1

Figure 1A:
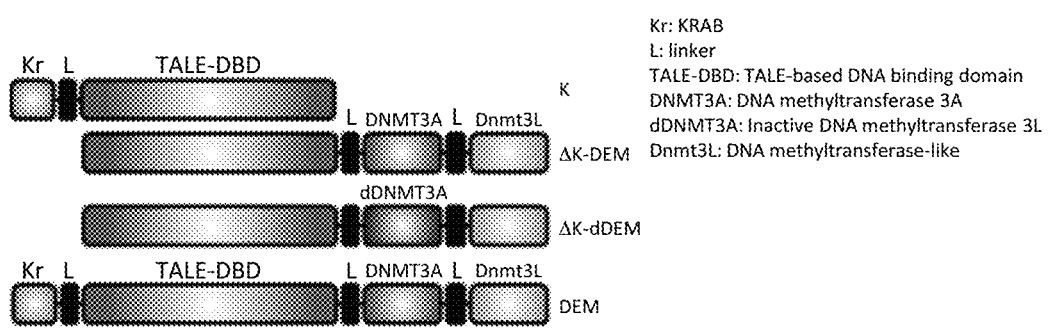
FIGS. 1A and 1B depict an designer epigenome modifier (DEM) and mechanism of action.
Figure 1B:
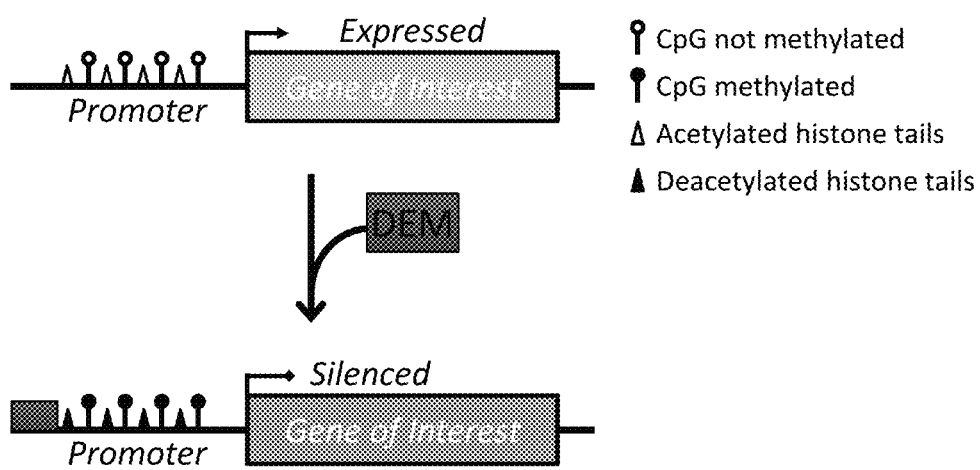

The ability to modulate the expression of target genes at will is a major need in the field of gene therapy. The present invention allows precise epigenome editing resulting in silencing of a target gene. The versatility of the platform concedes also that a silenced target gene can be transcriptionally reactivated by changing the combination of effector domains with transcription activator domains like herpes simplex virus-based transcriptional activator VP64 domain and DNA demethylase effectors from the TET family. The invention combines in a single molecule the highly specific DNA binding domain derived from transcription activator-like effectors (TALEs) identified in the plant pathogen *Xanthomonas* with the Krüppel-associated box (KRAB) domain, the human derived DNA methyltransferase 3a and the murine DNA methyltransferase 3L (FIG. 1A). The resulting construct also referred to as designer epigenome modifier or DEM, thereby combines the KRAB-induced recruitment of the scaffold protein KRAB-associated protein 1 (KAP1) that is suggested to regulate transcription through the induction of histone modifications as deacetylation or trimethylation with the DNA methylation ability of DNA methyltransferase 3A capable of covalently adding one CH3 group to cytosines within CpG dinucleotides. Activity of DNMT3A is further enhanced by the Dnmt3L component. Both histone deacetylation and DNA methylation are commonly associated with closed and silenced chromatin structures, thereby the introduction of these repressive epigenetic marks in a promoter or enhancer region will lead to transcriptional silencing of the target gene (FIG. 1B).

The single experimental steps were in general performed in the examples as described below unless deviations from the general procedures are explicitly mentioned:

a) Generation of TALE-based DEM plasmids. The TALE arrays targeted to the chosen CCR5 or CXCR4 sequences are generated using the platform described and can be cloned via Bpil restriction digestion using the different DEM plasmids depicted in FIG. 1A as Level 3 destination vectors. After ligation and transformation, colony PCR can be used to monitor for the successful cloning of the TALE-array. The positive colonies are expanded and plasmid DNA is extracted using a low-scale plasmid preparation kit. After sequence validation, the plasmids are further prepared using a large-scale plasmid purification kit.

b) In vitro mRNA transcription. For the in vitro transcription of an mRNA encoding for the different DEMs depicted in FIG. 1A, 10 μg of the corresponding expression plasmids are linearized with PspOMI restriction enzyme. The linearized plasmids are purified using the QIAquick PCR Purification Kit and 1 μg of linearized plasmid is used for in vitro transcription using the mMESSAGEmMACHINE™ T7 Ultra kit from ThermoFisher Scientific (Waltham, Mass.) that is designed for the in vitro synthesis of large amounts of capped RNA based on the T7 promoter. The T7 transcription reaction is performed for 2 h at 37° C. The mRNA encoding for the transgene of interest is recovered by lithium chloride precipitation as suggested by the provider and is subdivided in 2 μg aliquots and stored at −80° C.

c) Generation of HEK293T-based reporter cell line. The genomic region containing the DEM target site is amplified from human genomic DNA using a proof-reading polymerase. Upon purification, the amplicon is inserted in a lentiviral transfer plasmid via canonical molecular cloning. The lentiviral plasmid harboring the target site upstream of a minimal CMV promoter and the EGFP gene is subsequently used for the generation of a lentiviral vector as described. The vector is used to transduce HEK293T cells and three days after transduction, the cells are analyzed by flow cytometry to observe successful virus transduction and GFP expression. Sample showing low GFP expression (~10 GFP positive cells) indicative of low integrated copy number of the lentiviral vector are expanded for single cell sorting. A selected HEK293T-GFP clone is used for the experiments reported.

d) Reporter cell transfection and assessment of GFP silencing. HEK293T-GFP reporter cells are seeded 24 h before transfection and 2 μg of the mRNA coding for the indicated DEM construct are used for transfection using Lipofectamine® 2000 in optiMEM following the manufacturer instructions. The DEMs activity can be measured two days after transfection by analyzing the level of GFP expression via flow cytometry. Flow cytometry analysis is repeated at later time points to monitor the extent of stable silencing induced by DEMs.

e) Culturing, activation and nucleofection of primary human CD4+ T cells. CD4+ T cells are isolated from blood of normal individuals using magnetic beads. Activation beads containing antibodies recognizing CD2, CD3 and CD28 are prepared according to the manufacturer's instructions and mixed gently with the isolated CD4+ cells in a 2:1 (cells:beads) ratio. Three days later, the beads are removed using a magnet (namely the DynaMag™ 15 magnet from Invitrogen (Carlsbad, Calif.)), and the cells are ready for nucleofection. To this end, according to manufacturer's protocol for stimulated human T cells (Lonza), CD4+ T cells are mixed with nucleofection solution and with the mRNA encoding for the indicated DEM and nucleofected using the program EO-115. Cells are harvested 4 days later for qPCR and flow cytometry analysis. Afterwards, cells are re-activated to allow for long term culturing and later time point analysis (up to day 18 post thawing).

f) DNA methylation analysis via bisulfite sequencing. Genomic DNA is isolated from HEK293T-GFP or primary human T cells transfected with the indicated DEMs at the chosen time points via the QIAamp® DNA Blood Mini Kit, a DNA purification kit available from Thermo Fisher Scientific (Waltham, Mass.). Bisulfite conversion is performed on 500 ng of the purified genomic DNA with the EZ DNA Methylation Gold Kit following the instructions. To interrogate the methylation status of the CpG dinucleotides in a certain genomic location (on-targets or off-targets), the region of interest is amplified via PCR using the bisulfite converted DNA as template. Amplification is performed with the PyroMark™ PCR Kit, a PCR kit specifically optimized for pyrosequencing analysis available from QIAGEN (Hilden, Germany). PCR amplicon are cloned via the CloneJET PCR Cloning Kit into pJET plamid. To know the extent of CpG methylation, the pJET plasmids are sequenced via Sanger sequencing since sodium bisulfite conversion of the genomic DNA changes non methylated cytosines to uraciles leaving unaltered methylated cytosines. Thereby, Sanger sequencing can be used to distinguish the two different nucleotides that will appear as thymine if originally not methylated or as cytosine if originally methylated. In particular, CG to TG mutations represent non methylated cytosines whereas the presence of a CG is indicative of methylated cytosines. For a more quantitative analysis, PCR amplicons are also sequenced via next generation sequencing (NGS).

g) Analysis of chromatin accessibility via ATAC-Seq. ATAC-Seq was performed as described. Library fragments were amplified with NEBNext® Ultra II Q5 Master Mix, a hot start formulation available from new England Biolabs Inc. (Ipswich, Mass.), and purified and size-selected with AMPure™ XP beads, proprietary SPRI paramagnetic decontaminations beads available from Beckman Coulter Lifesciences (Indianapolis, Ind.). Libraries were sequenced on a HiSeq™ 2000 system, an automated sequencing system available from Illumina, Inc. (San Diego, Calif.), as single reads. Reads were aligned to hg19 with Bowtie software (Johns Hopkins University). Two biological replicates were performed. Circos software package was used for visualization and the replicates were combined. The top ten potential off-targets were determined as 3-fold tag difference between the control and modified cells in both replicates, a minimum of 10 normalized tags in control cells and within 10-kb of TSS of active gene.

Example 2

In order to prove the efficacy of the invention CCR5 was used as exemplary target gene which is known to be essential for infection of CD4+ T cells with the human immunodeficiency virus (HIV). Individuals that harbor natural mutations inactivating the CCR5 gene are largely resistant to HIV infection. DEMs targeted to the CCR5 promoter were generated and to test their activity, a fluorescent reporter harboring an enhanced green fluorescent protein (eGFP) gene driven by a minimal CMV (minCMV) promoter fused to a fragment of the CCR5 promoter containing the DEM target sites was prepared. The reporter was integrated in the genome of HEK293T cell line via lentiviral transduction resulting in a cell line expressing GFP (green fluorescent proteins) under the control of the CCR5-minCMV fusion promoter (FIG. 2A). Delivery of effectors having only the KRAB domain or only the DNA methyltransferase domains resulted in a transient silencing of the eGFP gene expression which came back to normal after two weeks in culture. However, upon delivery of mRNA encoding for DEMs, the eGFP expression was silenced in about 80% of cells with a very fast kinetics (i.e. after only 6 days) and remained stable over time up to two months post mRNA delivery (FIG. 2B). Importantly, although delivering the different effectors in a separate fashion, meaning the KRAB in one molecule and the DNA methyltransferases DNMT3A and Dnmt3L in a second molecule binding to two adjacent sites, resulted in eGFP silencing, the extent of eGFP silencing was lower than when a single construct, i.e. a DEM, was used (FIG. 2B, see sample indicated with "ΔKDEM #6+K #3").

This experiment clearly shows the advantage of using a single molecule DEM over multiple molecules targeting adjacent sites. Importantly, the eGFP silencing induced by DEM could be reverted by using DNA demethylating agents, as 5-AZA (FIG. 2C), but not using transient activators (i.e. a TALE-DBD fused to a VP64 activator domain) highlighting that silencing is indeed due to specific methylation of the eGFP promoter. Bisulfite sequencing was used to determine the extent of induced CpG methylation and to define the window in which methylation occurred. To this end, genomic DNA was extracted from the reporter cell line one month after DEM delivery and was converted using bisulfite reaction. This leads to conversion of all non-methylated cytosines into thymine while methylated cytosines remain unaltered. Upon PCR amplification of regions at variable distance from the DEM binding site and subsequent sequencing, we assessed that up to 80% of the CpG resulted methylated as compared to control and the levels of methylation were reduced to 40-60% at 2-kb distance from the DEM binding site (FIG. 2D). This experiment unequivocally shows that silencing mediated by DEM is indeed due to target DNA methylation and that the long term effect can be achieved by a single administration of an mRNA molecule encoding for the DEM.

Example 3

To prove that the invention is easily scalable to different genes, four TALE-based DNA binding domains were constructed targeting the CXCR4 gene (FIG. 3A) with the aim to silence also the second co-receptor used by the HIV to infect the target CD4+ T cells. The CXCR4-specific TALE-DBDs were incorporated in the different construct depicted in FIG. 1A and delivered in form of mRNA into HEK293T cells. Three days after lipofection of the mRNA, the levels of CXCR4 transcripts were measured via qPCR. Interestingly, all four CXCR4-specific DEMs reduced 4- to 5-folds the CXCR4 transcripts levels with an average reduction of about 70% in gene expression (FIG. 3B). Similarly, protein levels measured via flow cytometry were also reduced to the same extent (FIG. 3C).

Example 4

To test the therapeutic relevance of the invention, its potency was assessed in normal human CD4+ T cells isolated from blood of healthy donor. After isolation, cells were activated for three days prior nucleofection with mRNA encoding CCR5- or CXCR4-specific DEMs (FIG. 4A). To increase the potency, combinations of multiple DEMs targeting the same locus at a neighboring target sequence were tested. Four days after nucleofection, part of the cells were harvested for analyzing CCR5 or CXCR4 mRNA levels via qPCR and their corresponding protein levels via flow cytometry. CD4+ T cells express very high levels of CXCR4 as compared to CCR5. Indeed, four days after nucleofection, effect of DEMs was particularly evident at the CCR5 locus (both mRNA and protein) with a peak of 50% reduction in expression levels as compared to control by using a combination of two DEMs (FIGS. 4B and 4C, upper left graphs), while CXCR4 levels were only mildly affected (FIGS. 4B and 4C, upper right graphs). Delivering the effectors on two separate molecules had no effect in primary CD4+ T cells (FIGS. 4B and 4C, columns identified with "ΔK-DEM #6+K #3"). Cells were further activated and cultivated for two additional weeks to prove that DEMs induce long term epigenetic silencing of the target locus. Surprisingly, 18 days post nucleofection, the levels of CXCR4 were dramatically reduced of about 50% as compared to control (FIGS. 4B and 4C, lower right graphs). In contrast, CCR5 was re-activated in most of the cells (FIGS. 4B and 4C, lower left graphs) which is somewhat expected because the in vitro T cell activation procedure is necessary to keep the cells in culture and it does induce CCR5 expression, which may lead to selection of cells expressing CCR5.

Example 5

To prove that the silencing effect observed at four days post nucleofection was indeed due to increased methylation of the CCR5 promoter, the status of the CpG in a region of 9-Kb surrounding the CCR5-specific DEM target site was analyzed via bisulfite high throughput sequencing (FIG. 5A). Strikingly, we could observe increased CpG methylation in a 1-kb window surrounding the DEM binding site which was more pronounced in proximity of the target site (FIGS. 5B and 5C).

Example 6

To assess the propensity of DEMs to introduce off-targeted methylation, an assay for transposase-accessible chromatin using sequencing (ATAC-seq) was performed. This is a genome wide method to assess chromatin accessibility through the introduction of small sequence tags that are used for next generation sequence as readout for genomic accessibility (FIG. 6A).

It was hypothesized that off-target DNA methylation can reduce chromatin accessibility at potential off-target sites and thereby reduce the introduction of tags at those sites. Four days after nucleofection of the mRNA encoding for the CCR5-specific DEM, cells were harvested and ATAC-seq revealed reduced accessibility at the CCR5 on-target site in a window of about 2-kb from the DEM binding site (FIG. 6B; upper panel). Interestingly, no differences were detected at an unrelated housekeeping gene (B2M, FIG. 6B; lower panel). The top 10 potential off-target sites in silico using the TAL Effector Nucleotide Targeter 2.0 online tool (Table 1) were predicted and the potential off-target methylation via high throughput bisulfite sequencing was analyzed.

No increase in CpG methylation at these sites except for the OT5 was observed (FIG. 7A). However, the already high level of CpG methylation in the control sample at this site and the poor accessibility measured via ATAC-Seq (FIG. 7B) suggest that this effect is not relevant. The off-target analysis was expanded by predicting in silico all the potential off-target sites harboring one or two mismatched nucleotides as compared to the on-target site using COSMID. A total of 53 potential off-target sites (Table 2) was identified. Importantly, at all these sites no decrease in DNA accessibility via ATAC-Seq was observed with most of them showing only poor chromatin accessibility suggesting that the nearest genes are not expressed in CD4+ T cells. This highlights the high safety profile associated with the use of DEMs.

TABLE 1

List of potential off-target sites identified with TAL Effector Nucleotide Targeter 2.0

| ID | Chr Strand | Gene | Mismatches | Score | Start Position | Target Sequence | Distance from TSS (bp) | COSMID score | Cosmid mismatch |
|----|------------|------|------------|-------|----------------|-----------------|------------------------|--------------|-----------------|
| 0 | 3 Plus | CCR5 | 0 | 4.98 | 464116596 | TGACCATATACTTATGTCA (SEQ ID NO: 15) | 19 | 0 | |
| 1 | 7 Plus | LOC101927668 | 2 | 6.24 | 20121800 | TAACCATATACTTATCTCA (SEQ ID NO: 16) | 42968 | ID #396 | ID #35 |
| 2 | 4 Plus | Intergenic | 1 | 7.31 | 165401212 | TGAACATATACTTATGTCA (SEQ ID NO: 17) | n/a | ID #1 | ID #1 |
| 3 | 18 Plus | YES1 | 2 | 8.04 | 779684 | TGACCATATACCTATCTCA (SEQ ID NO: 18) | 32626 | ID #567 | ID #40 |
| 4 | 17 Plus | Intergenic | 3 | 8.24 | 8563008 | TCACCATATACATATATCA (SEQ ID NO: 19) | n/a | ID #573 | ID #580 |
| 5 | 20 Plus | Intergenic | 3 | 8.24 | 12726816 | TCACCATATACATATATCA (SEQ ID NO: 20) | n/a | ID #575 | ID #582 |
| 6 | 5 Plus | Intergenic | 3 | 8.24 | 97609784 | TCACCATATACATATATCA (SEQ ID NO: 21) | n/a | ID #574 | ID #581 |
| 7 | 12 Plus | TEAD4 | 2 | 8.36 | 3076665 | TGAACATATACTTATCTCA (SEQ ID NO: 22) | 8186 | ID #405 | ID #36 |

TABLE 1-continued

List of potential off-target sites identified with TAL Effector Nucleotide Targeter 2.0

| ID | Chr | Strand | Gene | Mismatches | Score | Start Position | Target Sequence | Distance from TSS (bp) | COSMID score | Cosmid mismatch |
|---|---|---|---|---|---|---|---|---|---|---|
| 8 | 5 | Plus | LOC101927421 | 3 | 8.63 | 124565833 | TAACCATATATTTATATCA (SEQ ID NO: 23) | 193308 | ID #536 | ID #545 |
| 9 | X | Minus | Intergenic | 3 | 8.63 | 112150169 | TAACCATATATTTATATCA (SEQ ID NO: 24) | n/a | ID #535 | ID #544 |
| 10 | 2 | Minus | NYAP2 | 3 | 8.9 | 226408801 | TAGCCATATACTTATATCA (SEQ ID NO: 25) | 143199 | ID #427 | ID #440 |

TABLE 2

List of potential off-target sites identified with COSMID
(Ordered by number of mismatches)

| ID | Chr | Strand | Gene | Mismatches | Position | Target Sequence | Distance from TSS (bp) |
|---|---|---|---|---|---|---|---|
| 0 | 3 | plus | CCR5 | 0 | 46411595 | TGACCATATACTTATGTCA (SEQ ID NO: 26) | 19 |
| 1 | 4 | minus | Intergenic | 1 | 165401211 | TGAACATATACTTATGTCA (SEQ ID NO: 27) | n/a |
| 2 | 12 | minus | Intergenic | 2 | 126201878 | AGACAATATACTTATGTCA (SEQ ID NO: 28) | n/a |
| 3 | 4 | minus | Intergenic | 2 | 34747592 | TCACTATATACTTATGTCA (SEQ ID NO: 29) | n/a |
| 4 | 18 | plus | MIB1 | 2 | 19371552 | TTACAATATACTTATGTCA (SEQ ID NO: 30) | 86634 |
| 5 | 12 | plus | Intergenic | 2 | 66048068 | TGAGAATATACTTATGTCA (SEQ ID NO: 31) | n/a |
| 6 | 8 | minus | Intergenic | 2 | 111862001 | TGATTATATACTTATGTCA (SEQ ID NO: 32) | n/a |
| 7 | 13 | plus | SERP2 | 2 | 44968765 | TGAGCATCTACTTATGTCA (SEQ ID NO: 33) | 20787 |
| 8 | 17 | plus | Intergenic | 2 | 14261495 | TGACCCTCTACTTATGTCA (SEQ ID NO: 34) | n/a |
| 9 | 4 | minus | Intergenic | 2 | 106456883 | TGATCATATCCTTATGTCA (SEQ ID NO: 35) | n/a |
| 10 | 18 | minus | ATP9B | 2 | 76945488 | TTACCATATAGTTATGTCA (SEQ ID NO: 36) | 116094 |
| 11 | 3 | plus | KCNMB2 | 2 | 178293606 | TGTCCATATATTTATGTCA (SEQ ID NO: 37) | 16988 |
| 12 | 13 | plus | DCLK1 | 2 | 36353811 | TGACCAAATTCTTATGTCA (SEQ ID NO: 38) | 76169 |
| 13 | 8 | plus | Intergenic | 2 | 33669235 | TGATCATATAGTTATGTCA (SEQ ID NO: 39) | n/a |
| 14 | 6 | plus | C6orf203 | 2 | 107362597 | TGACTATATATTTATGTCA (SEQ ID NO: 40) | 13190 |
| 15 | 5 | plus | Intergenic | 2 | 160357986 | TGACCATTTGCTTATGTCA (SEQ ID NO: 41) | n/a |
| 16 | 7 | plus | Intergenic | 2 | 84533770 | TGACCAAATATTTATGTCA (SEQ ID NO: 42) | n/a |
| 17 | 11 | minus | Intergenic | 2 | 127541818 | TGACCATCTATTTATGTCA (SEQ ID NO: 43) | n/a |
| 18 | 8 | plus | Intergenic | 2 | 31056581 | TTACCATATACATATGTCA (SEQ ID NO: 44) | n/a |
| 19 | X | plus | Intergenic | 2 | 99230790 | TGTCCATATACATATGTCA (SEQ ID NO: 45) | n/a |
| 20 | 3 | minus | KIAA1257 | 2 | 128677399 | TGTCCATATACATATGTCA (SEQ ID NO: 46) | 35499 |
| 21 | 6 | plus | RNGTT | 2 | 89528614 | TGACCATACATTTATGTCA (SEQ ID NO: 47) | 144716 |
| 22 | 3 | minus | ST6GAL1 | 2 | 186686208 | TGACCGTATACATATGTCA (SEQ ID NO: 48) | 37896 |
| 23 | 10 | minus | Intergenic | 2 | 109301891 | TGAGCATATACTGATGTCA (SEQ ID NO: 49) | n/a |
| 24 | 1 | minus | Intergenic | 2 | 115995413 | TGACCATATGTTTATGTCA (SEQ ID NO: 50) | n/a |
| 25 | 8 | minus | TRPS1 | 2 | 116567819 | TGACCACATACTGATGTCA (SEQ ID NO: 51) | 113388 |
| 26 | 5 | minus | Intergenic | 2 | 13083831 | TGACCATACACTGATGTCA (SEQ ID NO: 52) | n/a |

TABLE 2-continued

List of potential off-target sites identified with COSMID
(Ordered by number of mismatches)

| ID | Chr | Strand | Gene | Mismatches | Strand Position | Target Sequence | Distance from TSS (bp) |
|---|---|---|---|---|---|---|---|
| 27 | 16 | minus | Intergenic | 2 | 61077413 | TTACCATATACTTTTGTCA (SEQ ID NO: 53) | n/a |
| 28 | 12 | plus | SCN8A | 2 | 52015830 | TGATCATATACTTCTGTCA (SEQ ID NO: 54) | 30810 |
| 29 | X | minus | Intergenic | 2 | 98322767 | TGATCATATACTTTTGTCA (SEQ ID NO: 55) | n/a |
| 30 | 13 | minus | Intergenic | 2 | 48720381 | TGACCTTATACTTCTGTCA (SEQ ID NO: 56) | n/a |
| 31 | 8 | minus | PXDNL | 2 | 52364466 | TGACCATCTACTTGTGTCA (SEQ ID NO: 57) | 357518 |
| 32 | 10 | plus | JMJD1C | 2 | 65030745 | TGGCCATATACTTAAGTCA (SEQ ID NO: 58) | 194959 |
| 33 | 1 | plus | Intergenic | 2 | 81197612 | TGACCAAATACTTAGGTCA (SEQ ID NO: 59) | n/a |
| 34 | X | plus | REPS2 | 2 | 17017334 | TGACCATATACATGTGTCA (SEQ ID NO: 60) | 52520 |
| 35 | 7 | plus | LOC101927668 | 2 | 20121799 | TAACCATATACTTATCTCA (SEQ ID NO: 61) | 58232 |
| 36 | 12 | plus | TEAD4 | 2 | 3076664 | TGAACATATACTTATCTCA (SEQ ID NO: 62) | 8186 |
| 37 | 4 | minus | METTL14 | 2 | 119610622 | TGACCATAAACTTATTTCA (SEQ ID NO: 63) | 4'051 |
| 38 | 12 | minus | DDX47 | 2 | 12967242 | TGACCATATCCTTATTTCA (SEQ ID NO: 64) | 1104 |
| 39 | 10 | minus | TCTN3 | 2 | 97447765 | TGACCATATTCTTATCTCA (SEQ ID NO: 65) | 6114 |
| 40 | 18 | plus | YES1 | 2 | 779683 | TGACCATATACCTATCTCA (SEQ ID NO: 66) | 32626 |
| 41 | 2 | minus | Intergenic | 2 | 224060353 | TGACAATATACTTATGACA (SEQ ID NO: 67) | n/a |
| 42 | 1 | minus | NEGR1 | 2 | 72084753 | TGACCATATCCTTATGGCA (SEQ ID NO: 68) | 481840 |
| 43 | Y | minus | Intergenic | 2 | 17815850 | TGACCATATAATTATGCCA (SEQ ID NO: 69) | n/a |
| 44 | 9 | minus | LINGO2 | 2 | 29004177 | TGAGCATATACTTATGTAA (SEQ ID NO: 70) | 208800 |
| 45 | 10 | plus | Intergenic | 2 | 47982402 | TGACCATGTACTTATGTAA (SEQ ID NO: 71) | n/a |
| 46 | 10 | plus | Intergenic | 2 | 51927697 | TGACCATGTACTTATGTAA (SEQ ID NO: 72) | n/a |
| 47 | 10 | minus | Intergenic | 2 | 52532086 | TGACCATGTACTTATGTAA (SEQ ID NO: 73) | n/a |
| 48 | 5 | plus | PRLR | 2 | 35132581 | TGACCATATTCTTATGTAA (SEQ ID NO: 74) | 98092 |
| 49 | 20 | minus | Intergenic | 2 | 12544854 | TGACCATATAGTTATGTAA (SEQ ID NO: 75) | n/a |
| 50 | 2 | plus | Intergenic | 2 | 47956567 | TGACCATATACGTATGTAA (SEQ ID NO: 76) | n/a |
| 51 | 11 | plus | BDNF | 2 | 27732515 | TGACTATATACTTATGTCT (SEQ ID NO: 77) | 8761 |
| 52 | 7 | plus | Intergenic | 2 | 134102729 | TGACCATATTCTTATGTCT (SEQ ID NO: 78) | n/a |
| 53 | X | minus | Intergenic | 2 | 119842107 | TGACCATATACTTTTGTGA (SEQ ID NO: 79) | n/a |

Example 7

HEK293T cells were transfected with mRNA coding for the indicated (active or inactive) DEM using Lipofectamine. As a result of CXCR4-specific DEM activity, CpGs within the CXCR4 promoter were methylated and CXCR4 gene was silenced. In detail, the genomic DNA which is isolated from cells transfected either with inactive (ΔK-dDEM #L1) or active (DEM #R2) epigenetic effectors is subjected to bisulfite conversion. Under this condition, methylated CGs remain CGs while unmethylated CGs are converted to TAs.

HEK293T cells were harvested 20 days post transfection and CpG methylation assessed by bisulfite sequencing at a distance of −300 bp to +100 bp relative to the binding site R2 indicated (mean±S.E.M., n=4). After bisulfite treatment, the genomic DNA was used as a template for PCR to amplify the four regions indicated with numbers from #1 to #4 in FIG. 8A. The 8 amplicons (four from cells transfected with inactive and four from those transfected with active epigenetic effector) were sequenced and CpG methylation was calculated as average per each amplicon.

In FIG. 8A, the CXCR4 locus is shown schematically with the four amplicons investigated for the extent of CpG methylation indicated in scale and numbered from #1 to #4.

In FIG. 8B, the graph depicts the level of CpG methylation in cells receiving the active or inactive DEM respectively. Statistical significance was calculated with a two-tailed, paired Student's t-test (*P<0.05; **P<0.01).

Example 8

CXCR4-expression levels was measured on day 2 and day 22 after delivery of the CXCR4-specific DEMs in HEK293T cells and the corresponding results are shown in FIG. 9.

The histograms show the CXCR4 expression levels upon delivery of the different effectors targeting to the CXCR4 promoter and indicated with letters from A to D. CXCR4 transcript levels, normalized to the housekeeping gene B2M, are expressed relative to the corresponding inactive control in A (mean±S.E.M., experiments were performed three times in triplicate). Statistical significance calculated with a two-tailed, paired Student's t-test (**P<0.01).

In this experiment HEK293T cells were transfected with mRNA coding for the indicated DEM using Lipofectamine. As a result of DEM activity, CpGs within the CXCR4 promoter were methylated and CXCR4 gene is silenced. CXCR4 expression levels were measured via quantitative RT-PCR (TaqMan) at the indicated time points as shown in FIG. 9 (Day 2, grey bars; Day 22, white bars). The histogram shows the extent of CXCR4 gene expression as compared to the samples transfected with mRNA coding for the inactive ΔK-dDEM #R2 (Indicated with letter "A"). The gene expression levels are normalized to the housekeeping gene B2M. In this experiment, the efficacy of different effectors is compared showing that the subject of this patent application (DEM, indicated with the letter "D") in this case targeting the promoter of the CXCR4 gene is able to induce target gene silencing long term. This experiment proves that the DEMs disclosed herein can be used successfully in practical applications.

Example 9

Primary human T cells were harvested 21 days post transfection and CpG methylation assessed by bisulfite sequencing at a distance of −300 bp to +100 bp relative to the binding site R2 indicated (mean±S.E.M., n=4). The results are shown in FIGS. 10A and 10B.

In FIG. 10A, the CXCR4 locus is shown schematically with the four amplicons investigated for the extent of CpG methylation indicated in scale and numbered from #1 to #4.

In FIG. 10B, the graph depicts the level of CpG methylation in cells receiving the active or inactive DEM respectively. Statistical significance was calculated with a two-tailed, paired Student's t-test (*P<0.05; **P<0.01).

The method was the same as in Example 7, but different cells (no cell line but primary T cells from human donors) were used. Primary human T cells were transfected with mRNA coding for the indicated DEM using Nucleofection. As a result of DEM activity, CpGs within the CXCR4 promoter are methylated and the CXCR4 gene is silenced. In detail, the genomic DNA is isolated from cells transfected either with inactive (ΔK-dDEM #L1) or active (DEM #R2) epigenetic effector and subjected to bisulfite conversion. Under this condition, methylated CGs remain CGs while unmethylated CGs are converted to TAs. After bisulfite treatment, the genomic DNA was used as a template for PCR to amplify the four regions indicated with numbers from #1 to #4 in the upper panel of the figure. The 8 amplicons (four from cells transfected with inactive and four from those transfected with active epigenetic effector) are sequenced and CpG methylation is calculated as average per each amplicon.

Example 10

FIGS. 11A-11O depict the deposition of the repressive epigenetic mark H3K9me3 in close proximity of the CCR5-specific DEM #6 (A) or CXCR4-specific DEM #R2 (B) binding sites respectively.

FIGS. 11A and 11B indicate the DEM binding sites (horizontal bars on top) and the position of the investigated amplicons are shown to scale below the analyzed gene with reference to the genomic locus.

Cells were harvested seven days post nucleofection and H3K9me3 ChIP analysis carried out. Results are depicted in FIG. 11O, expressed as the percentage of input relative to actin.

UNTR5 was used as a positive control (mean±S.E.M., n=3). Statistical significance calculated with a two-tailed, paired Student's t-test (*P<0.05).

In the experiment, HEK293T cells were fixed with formaldehyde to block proteins on DNA. Subsequently genomic DNA was destroyed into small fragments via sonication. The fragmented genomic DNA complexed to proteins was purified and then incubated with an antibody recognizing the repressive epigenetic mark H3K9me3 protein. The complex of DNA+protein+Antibody was then purified and the amount of DNA quantified via qRT-PCR for the indicated regions. An increase in PCR signal was an indirect measurement of the levels of repressive epigenetic mark in the analyzed DNA region.

Example 11

FIG. 12 schematically depicts the specificity profiles of DEMs. FIG. 12 is a Venn diagram showing the overlap between ATAC-seq, RNA-seq and in silico off-target sites predicted via COSMID (as shown in Table 2). The number of overlapping sites is indicated. Overlap with computational prediction of off-target sites is restricted to hits within 10-kb distance from the annotated transcription start sites (TSS) of the 84 de-regulated genes identified via RNA-seq analysis or from the 325 regions of lower chromatin accessibility resulting from ATAC-seq analysis, respectively.

For RNA-seq, primary human T cells nucleofected either with mRNA encoding for active or inactive CCR5-specific DEM from three independent experiments were harvested and RNA extracted. Further analysis including whole transcriptome sequencing and bioinformatics was performed.

For ATAC-seq, primary human T cells nucleofected either with mRNA encoding for active or inactive CCR5-specific DEM from two independent experiments were harvested and genomic DNA extracted. Accessible chromatin was marked by "Tagmentation" and then fragmented. These fragments were then sequenced via high throughput sequencing and bioinformatic analysis performed to identify regions of lower chromatin accessibility based on the relative abundance of sequence reads in the two sets of samples (nucleotected with active Vs. inactive CCR5-specific DEM). Results are shown schematically in FIG. 12.

To further investigate the off target effect of DEM delivery in primary human T cells, total RNA extracted from three independent experiments was subjected to whole transcriptome analysis via RNA-seq and the results are shown in FIG. 12.

CCR5 transcript levels were reduced up to 1.7-fold while no differences were measured at the unrelated β2-microglobulin (B2M) gene. A more detailed analysis revealed 84 genes (including CCR5) that were consistently up- (28 genes) or down-regulated (56 genes) >1.5-fold.

To verify whether the observed de-regulation of the 84 genes was due to direct binding of CCR5-specific DEM #6 at off-target sites, the in silico analysis was expanded to all potential off-target sites harboring up to two mismatches as compared to the CCR5 on-target sequence using the online COSMID tool (Table 2). Importantly, none of the predicted off-target sites was within 10-kb of the transcription start sites of the differentially regulated transcripts. It can be concluded that the variations in gene expression measured by RNA-seq were unrelated to DEM off-target binding.

Further, ATAC-seq analysis previously shown for the top 10 off target sites was extended genome wide to identify all the sites with lower chromatin accessibility in cells receiving CCR5-specific DEM #6. 325 sites showing lower chromatin accessibility were identified. However, except for CCR5, none of these sites included any of the de-regulated genes identified via RNA-seq. Notably, none of the 324 regions showing lower chromatin accessibility had a predicted off-target site within 10-kb distance identified by COSMID (Table 2).

What is claimed:

1. A single molecule for stably silencing expression of a target gene of interest that is endogenous to a human primary cell via targeted epigenomic modification, said molecule comprising a fusion protein or a nucleic acid encoding said fusion protein, wherein said fusion protein comprises the following components:
   a) a Krüppel-associated box (KRAB) effector domain,
   b) a DNA binding domain capable of binding to said target gene,
   c) a human DNA methyltransferase DNMT3A or a homolog thereof that exhibits at least 90% sequence identity to SEQ ID NO: 3, and
   d) a murine DNA methyltransferase Dnmt3L or a homolog thereof that exhibits at least 90% sequence identity to SEQ ID NO: 5,
whereby components a), b), c) and d) are linked to each other either directly or via at least one linker.

2. The molecule according to claim 1, characterized in that said single molecule is a fusion protein.

3. The molecule according to claim 1, characterized in that said single molecule is a nucleic acid molecule.

4. A vector comprising the molecule according to claim 3.

5. The vector according to claim 4, characterized in that said vector is derived from a lentivirus, an adenovirus or an adeno-associated virus.

6. The molecule according to claim 3, characterized in that said single molecule is an mRNA molecule that optionally further comprises one or more additional components selected from the group consisting of a 7-methylguanosine cap at the 5'-end, an artificial cap analogue at the 5'-end, a non-coding region at the 5'-end, a non-coding region at the 3'-end and a polyA tail at the 3'-end.

7. The molecule according to claim 3, characterized in that said nucleic acid molecule is a DNA molecule.

8. The single molecule of claim 1, wherein said target gene of interest is a human T-cell receptor selected from the group consisting of human immunodeficiency virus (HIV) co-receptors CCR5 and CXCR4.

9. The single molecule of claim 1, wherein said Krüppel-associated box (KRAB) effector domain is capable of recruiting KRAB-associated protein 1 (KAP 1) that, in turn induces histone modification.

10. The single molecule of claim 1, wherein said Krüppel-associated box (KRAB) effector domain comprises the amino acid sequence of SEQ ID NO: 1 or an amino acid sequence that is at least 90% identical to SEQ ID NO: 1.

11. The single molecule of claim 1, wherein said DNA binding domain capable of binding to said target gene of interest is a transcription-activator-like effector-based DNA binding domain (TALE-DBD) having the amino acid sequence of SEQ ID NO: 7 or an amino acid sequence that is at least 90% identical to the sequence of SEQ ID NO: 7.

12. A method for stably silencing expression of a target gene of interest that is endogenous to a human primary cell, said method comprising the steps of:
   (a) introducing a single molecule according to claim 1 into human primary cells; and
   (b) silencing the gene of interest in said human primary cells via epigenetic modification.

13. The method according to claim 12, wherein said single molecule is an mRNA molecule.

14. The method according to claim 13, wherein step (a) is performed ex vivo.

15. The method according to claim 12, wherein said human primary cells are isolated T lymphocytes, and said target gene of interest is a human T-cell receptor selected from the group consisting of HIV co-receptors CCR5 and CXCR4.

* * * * *